United States Patent
Tawada et al.

(10) Patent No.: US 6,699,995 B1
(45) Date of Patent: Mar. 2, 2004

(54) PROCESS FOR THE PREPARATION OF OXAZOLE DERIVATIVES

(75) Inventors: Hiroyuki Tawada, Takatsuki (JP); Norihiko Ohashi, Takatsuki (JP); Motoki Ikeuchi, Nishinomiya (JP)

(73) Assignee: Takeda Chemical Industries, Ltd., Osaka (JP)

( * ) Notice: Subject to any disclaimer, the term of this patent is extended or adjusted under 35 U.S.C. 154(b) by 33 days.

(21) Appl. No.: 10/088,415

(22) PCT Filed: Sep. 14, 2000

(86) PCT No.: PCT/JP00/06302

§ 371 (c)(1), (2), (4) Date: Mar. 18, 2002

(87) PCT Pub. No.: WO01/19806

PCT Pub. Date: Mar. 22, 2001

(30) Foreign Application Priority Data

Sep. 16, 1999 (JP) ............................................. 11-262470
Mar. 17, 2000 (JP) ......................................... 2000-081823

(51) Int. Cl.[7] .................... C07D 263/04; C07D 263/16
(52) U.S. Cl. ...................................... 548/229; 548/232
(58) Field of Search .................................. 548/232, 229

(56) References Cited

FOREIGN PATENT DOCUMENTS

WO          97/36882          10/1997

OTHER PUBLICATIONS

H. R. Khan et al., "Some Novel Reactions of 2–Amino–4–methyloxazole with Aldehydes: Aryl and Alkyl Hydroxymethylation oat C–5", J. Heterocyclic Chem. 25 (3), pp. 815–817, 1988.

B. Mekonnen et al., "Friedel–Crafts Reactions of 2–Amino–4–(alkyl or aryl)oxazoles with Acid Chlorides and Acid Anhydrides: Synthesis of 5–Acyl–2–amino–4–alkyloxazoles", J. Heterocyclic Chem. vol. 34, No. 2, pp. 567–572, 1997.

*Primary Examiner*—Joseph K. McKane
*Assistant Examiner*—Andreä D. Small
(74) *Attorney, Agent, or Firm*—Wenderoth, Lind & Ponack, L.L.P.

(57) ABSTRACT

A production method of a compound represented by the formula

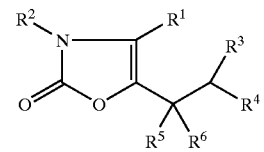

wherein $R^1$ and $R^2$ are each a hydrogen atom, an optionally substituted hydrocarbon group or an optionally substituted heterocyclic group, $R^3$ is an electron-withdrawing group, and $R^4$, $R^5$ and $R^6$ are each a hydrogen atom or an optionally substituted hydrocarbon group, or a salt thereof, is provided as an industrially advantageous production. method for forming a carbon-carbon bond at the 5-position of oxazole, which method includes reacting a compound represented by the formula

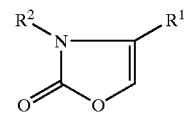

wherein the symbols in the formula are as defined above, or a salt thereof, with a compound represented by the formula

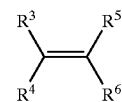

wherein the symbols in the formula are as defined above, or a salt thereof, in the presence of an acid or a base.

13 Claims, No Drawings

US 6,699,995 B1

PROCESS FOR THE PREPARATION OF OXAZOLE DERIVATIVES

This application is a 371 of PCT/JP00/06302 filed Sep. 14, 2000.

TECHNICAL FIELD

The present invention relates to an industrially advantageous production method for forming a carbon-carbon bond at the 5-position of oxazole.

BACKGROUND ART

There are various production methods (e.g. WO97/36882) of compounds having a carbon substituent (a group bonded via a carbon) bonded at the 5-position of oxazole. Most of them require introduction of a necessary carbon substituent before constructing an oxazole ring. However, the starting material usable for the production method is limited and the synthesis thereof is associated with difficulty.

In view of the above, the development of an easy and simple method for introducing a carbon substituent into the 5-position of oxazole is highly significant, and finding of a reaction permitting direct formation of a carbon-carbon bond on an oxazole having no substituent at the 5-position is extremely significant.

DISCLOSURE OF INVENTION

The present inventors have conducted intensive studies in an attempt to introduce a carbon substituent into the 5-position of oxazole and found for the first time that a reaction of an oxazole having no substituent at the 5-position (particularly one having an oxo group or amino group at the 2-position) with olefin in the presence of an acid or base unexpectedly results in an easy reaction with the olefin and the formation of a carbon-carbon bond at the 5-position of the oxazole, based on which they investigated further and completed the present invention.

Accordingly, the present invention relates to:

(1) a method of producing a compound represented by the formula

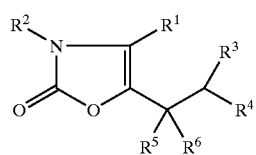

(III)

wherein
$R^1$ and $R^2$ are each a hydrogen atom, an optionally substituted hydrocarbon group or an optionally substituted heterocyclic group,
$R^3$ is an electron-withdrawing group, and
$R^4$, $R^5$ and $R^6$ are each a hydrogen atom or an optionally substituted hydrocarbon group, or a salt thereof, which method comprises reacting a compound represented by the formula

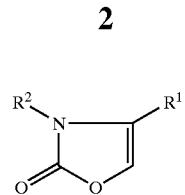

(I)

wherein the symbols in the formula are as defined above, or a salt thereof, with a compound represented by the formula

(II)

wherein the symbols in the formula are as defined above, or a salt thereof, in the presence of an acid or a base;
(2) the production method of the aforementioned (1), wherein $R^1$ and $R^2$ are each a hydrogen atom, an optionally substituted alkyl group, an optionally substituted aralkyl group, an optionally substituted aryl group or an optionally substituted heterocyclic group;
(3) the production method of the aforementioned (1), wherein $R^1$ is an optionally substituted aryl group or an optionally substituted aromatic heterocyclic group;
(4) the production method of the aforementioned (1), wherein $R^1$ is an optionally substituted phenyl group;
(5) the production method of the aforementioned (1), wherein $R^2$ is a hydrogen atom;
(6) the production method of the aforementioned (1), wherein $R^4$, $R^5$ and $R^6$ are each a hydrogen atom, an optionally substituted alkyl group or an optionally substituted aryl group;
(7) the production method of the aforementioned (1), wherein $R^4$, $R^5$ and $R^6$ are each a hydrogen atom;
(8) the production method of the aforementioned (1), wherein $R^3$ is —CN, —COOR$^7$ ($R^7$ is a hydrogen atom or an optionally substituted hydrocarbon group) or —COR$^8$ ($R^8$ is a hydrogen atom, an optionally substituted hydrocarbon group or an optionally substituted heterocyclic group);
(9) the production method of the aforementioned (1), wherein $R^3$ is —CN;
(10) the production method of the aforementioned (1), wherein $R^3$ is —COOR$^7$ ($R^7$ is a hydrogen atom or an optionally substituted alkyl group);
(11) the production method of the aforementioned (1), wherein $R^3$ is —COR$^8$ ($R^8$ is a hydrogen atom, an optionally substituted alkyl group or an optionally substituted aryl group);
(12) the production method of the aforementioned (1), wherein the reaction is carried out in the presence of an acid;
(13) a method of producing a compound represented by the formula

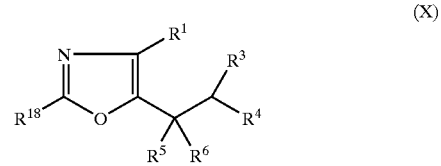

(X)

wherein
R$^1$ is a hydrogen atom, an optionally substituted hydrocarbon group or an optionally substituted heterocyclic group,
R$^{18}$ is an optionally substituted amino group, and other symbols are as defined above, or a salt thereof, which method comprises reacting a compound represented by the formula

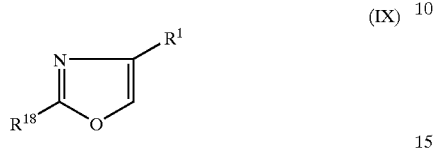

(IX)

wherein the symbols in the formula are as defined above, or a salt thereof, with a compound represented by the formula (II) or a salt thereof, in the presence of an acid;

(14) a method of producing a compound represented by the formula

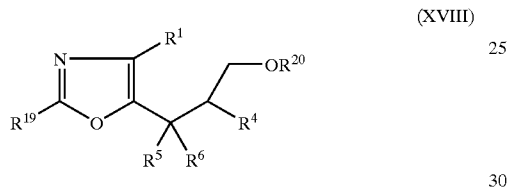

(XVIII)

wherein
R$^1$ is as defined above,
R$^4$, R$^5$, R$^6$ are each a hydrogen atom or an optionally substituted hydrocarbon group,
R$^{19}$ is an optionally substituted heterocyclic group containing nitrogen, which is bonded via a nitrogen atom, and
R$^{20}$ is an optionally substituted hydrocarbon group, or a salt thereof, which method comprises reacting a compound represented by the formula (I) or a salt thereof with a compound represented by the formula

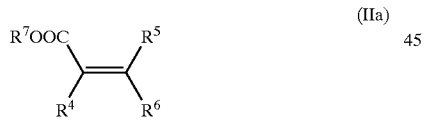

(IIa)

wherein R$^7$ is a hydrogen atom or an optionally substituted hydrocarbon group, and other symbols are as defined above, or a salt thereof, in the presence of an acid or a base to give a compound represented by the formula

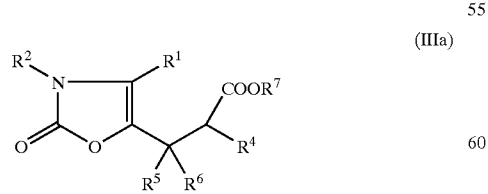

(IIIa)

wherein the symbols in the formula are as defined above, or a salt thereof, subjecting this compound to halogenation reaction to give a compound represented by the formula

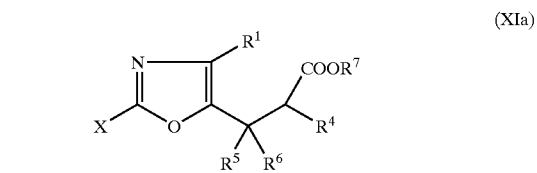

(XIa)

wherein X is a halogen atom, and other symbols are as defined above, or a salt thereof, reacting this compound with a compound represented by the formula: R$^{19}$—H (XII) [R$^{19}$ is as defined above] to give a compound represented by the formula

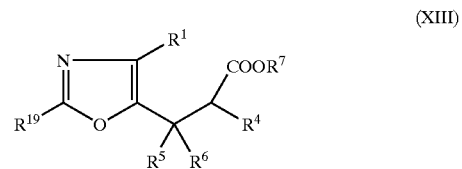

(XIII)

wherein the symbols in the formula are as defined above, or a salt thereof, subjecting this compound to a reduction reaction to give a compound represented by the formula

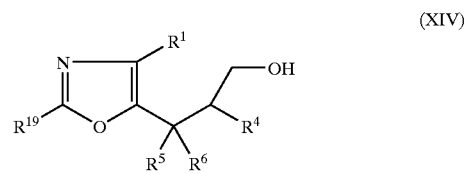

(XIV)

wherein the symbols in the formula are as defined above, or a salt thereof, reacting this compound with a compound represented by the formula: R$^{10}$SO$_2$Cl (XV) [R$^{10}$ is an optionally substituted alkyl group or an optionally substituted aryl group] or a halogenating agent to give a compound represented by the formula

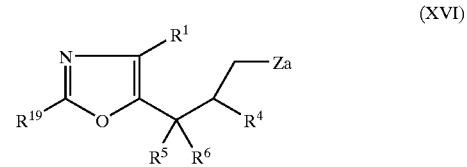

(XVI)

wherein Za is a halogen atom or —OSO$_2$R$^{10}$ (R$^{10}$ is as defined above), and other symbols are as defined above, or a salt thereof, and reacting this compound with a compound represented by the formula: R$^{20}$—OH (XVII) [R$^{20}$ is as defined above];

(15) a method of producing a compound represented by the formula (XVIII) or a salt thereof, which comprises reacting a compound represented by the formula (IX) or a salt thereof with a compound represented by the formula (IIa) or a salt thereof in the presence of an acid to give a compound represented by the formula

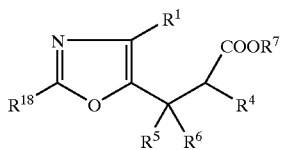

(Xa)

wherein the symbols in the formula are as defined above, or a salt thereof, subjecting this compound to halogenation reaction to give a compound represented by the formula (XIa) or a salt thereof, reacting this compound with a compound represented by the formula (XII) to give a compound represented by the formula (XIII) or a salt thereof, subjecting this compound to a reduction reaction to give a compound represented by the formula (XIV) or a salt thereof, reacting this compound with a compound represented by the formula (XV) or halogenating agent to give a compound represented by the formula (XVI) or a salt thereof, and reacting this compound with a compound represented by the formula (XVII);

(16) methyl. 4-(4-chlorophenyl)-2-(2-methylimidazol-1-yl)-5-oxazolepropionate; and the like.

The "hydrocarbon group" of the above-mentioned "optionally substituted hydrocarbon group" represented by $R^1$, $R^2$, $R^4$, $R^5$, $R^6$, $R^7$ or $R^8$ is exemplified by aliphatic hydrocarbon group, alicyclic hydrocarbon group, aryl group, aralkyl group and the like.

Examples of the aliphatic hydrocarbon group include linear or branched aliphatic hydrocarbon group having 1 to 15 carbon atom(s), such as alkyl group, alkenyl group, alkynyl group and the like, with preference given to alkyl group.

Preferable examples of alkyl group include alkyl group having 1 to 10 carbon atom(s) (preferably alkyl group having 1 to 6 carbon atom(s)), such as methyl, ethyl, propyl, isopropyl, butyl, isobutyl, sec.-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Preferable examples of alkenyl group include alkenyl group having 2 to 10 carbon atoms, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferable examples of alkynyl group include alkynyl group having 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The above-mentioned aliphatic hydrocarbon group may have the same or different, 1 to 5, preferably 1 to 3, substituent(s) at substitutable position(s). Examples of the substituent include (i) halogen atom (e.g., fluorine, chlorine, bromine, iodine and the like), (ii) $C_{1-6}$ alkoxy group (e.g., methoxy, ethoxy, propoxy, isopropoxy, n-butoxy, isobutoxy, sec-butoxy, tert-butoxy and the like), (iii) hydroxy group, (iv) amino group, (v) mono- or di-$C_{1-6}$ alkylamino group (e.g., methylamino, ethylamino, dimethylamino, diethylamino, methylethylamino and the like), (vi) nitro group, (vii) carboxyl group, (viii) $C_{1-6}$ alkoxy-carbonyl group (e.g., methoxycarbonyl, ethoxycarbonyl, tert-butoxycarbonyl and the like), (ix) $C_{1-6}$ alkyl-carbonyl group (e.g., methylcarbonyl, ethylcarbonyl, butylcarbonyl and the like), (x) benzoyl group, (xi) phenyl group, (xii) phenoxy group, (xiii) benzyloxy group and the like.

Examples of the alicyclic hydrocarbon group include saturated or unsaturated alicyclic hydrocarbon group having 3 to 12 carbon atoms, such as cycloalkyl group, cycloalkenyl group, cycloalkadienyl group and the like (preferably cycloalkyl group).

Preferable examples of cycloalkyl group include cycloalkyl group having 3 to 10 carbon atoms (preferably cycloalkyl group having 3 to 8 carbon atoms), such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferable examples of cycloalkenyl group include cycloalkenyl group having 3 to 10 carbon atoms, such as 2-cyclopenten-1-yl, 3-cyclopenten-1-yl, 2-cyclohexen-1-yl, 3-cyclohexen-1-yl and the like.

Preferable examples of cycloalkadienyl group include cycloalkadienyl group having 4 to 10 carbon atoms, such as 2,4-cyclopentadien-1-yl, 2,4-cyclohexadien-1-yl, 2,5-cyclohexadien-1-yl and the like.

The above-mentioned alicyclic hydrocarbon group may have the same or different, 1 to 5, preferably 1 to 3, substituent(s) at substitutable position(s). Examples of the substituent include (i) halogen atom (e.g., fluorine, chlorine, bromine, iodine and the like), (ii) $C_{1-6}$ alkoxy group (e.g., methoxy, ethoxy, propoxy, isopropoxy, n-butoxy, isobutoxy, sec-butoxy, tert-butoxy and the like), (iii) hydroxy group, (iv) amino group, (v) mono- or di-$C_{1-6}$ alkylamino group (e.g., methylamino, ethylamino, dimethylamino, diethylamino, methylethylamino and the like), (vi) nitro group, (vii) carboxyl group, (viii) $C_{1-6}$ alkoxy-carbonyl group (e.g., methoxycarbonyl, ethoxycarbonyl, tert-butoxycarbonyl and the like), (ix) $C_{1-6}$ alkyl-carbonyl group (e.g., methylcarbonyl, ethylcarbonyl, butylcarbonyl and the like), (x) benzoyl group, (xi) phenyl group, (xii) phenoxy group, (xiii) benzyloxy group and the like.

The aryl group is exemplified by aryl group having 6 to 14 carbon atoms, such as phenyl, naphthyl, anthryl, phenanthryl, acenaphthylenyl and the like. Of these, phenyl, 1-naphthyl, 2-naphthyl and the like are preferable.

The aralkyl group is exemplified by $C_{6-14}$ aryl-$C_{1-6}$ alkyl group, such as benzyl, 1-phenylethyl, 2-phenylethyl, 1-phenylpropyl, 2-phenylpropyl, 3-phenylpropyl,-1-naphthylmethyl, 2-naphthylmethyl and the like. Of these, phenyl-$C_{1-4}$ alkyl group and the like are preferable.

The above-mentioned aryl group and aralkyl group may have the same or different, 1 to 5, preferably 1 to 3, substituent(s) at substitutable position(s). Examples of the substituent include (i) $C_{1-3}$ alkylenedioxy group (e.g., methylenedioxy, ethylenedioxy and the like), (ii) nitro group, (iii) cyano group, (iv) carboxyl group, (v) $C_{1-6}$ alkoxy-carbonyl group (e.g., methoxycarbonyl, ethoxycarbonyl, tert-butoxycarbonyl and the like), (vi) hydroxy group, (vii) halogen atom (e.g., fluorine, chlorine, bromine, iodine and the like), (viii) optionally halogenated $C_{1-6}$ alkyl group (e.g., methyl, ethyl, propyl, isopropyl, n-butyl, isobutyl, sec-butyl, tert-butyl, trifluoromethyl and the like), (ix) $C_{1-6}$ alkoxy group (e.g., methoxy, ethoxy, propoxy, isopropoxy, n-butoxy, isobutoxy, sec-butoxy, tert-butoxy and the like), (x) benzyloxy group, (xi) phenyl group, (xii) benzoyl group, (xiii) phenoxy group, (xiv) amino group, (xv) mono- or di-$C_{1-6}$ alkylamino group (e.g., methylamino, ethylamino, dimethylamino, diethylamino, methylethylamino and the like), (xvi) $C_{1-6}$ alkyl-carbonyl group (e.g., methylcarbonyl, ethylcarbonyl, butylcarbonyl and the like) and the like.

The "heterocyclic group" of the above-mentioned "optionally substituted heterocyclic group" represented by $R^1$, $R^2$ or $R^8$ is exemplified by 5 to 10-membered aromatic heterocyclic groups such as pyridyl (e.g., 2-pyridyl, 3-pyridyl, 4-pyridyl etc.), pyrimidinyl (e.g., 2-pyrimidinyl, 5-pyrimidinyl, 6-pyrimidinyl etc.), pyridazinyl (e.g., 3-pyridazinyl, 4-pyridazinyl etc.), pyrazinyl (e.g., 2-pyrazinyl etc.), pyrrolyl (e.g., 1-pyrrolyl, 2-pyrrolyl etc.), imidazolyl (e.g., 1-imidazolyl, 2-imidazolyl, 4-imidazolyl, 5-imidazolyl etc.), pyrazolyl (e.g., 1-pyrazolyl, 3-pyrazolyl, 4-pyrazolyl etc.), isoxazolyl, isothiazolyl, thiazolyl (e.g., 2-thiazolyl, 4-thiazolyl, 5-thiazolyl etc.), oxazolyl (e.g., 2-oxazolyl, 4-oxazolyl, 5-oxazolyl etc.), 1,2,4-oxadiazolyl (e.g., 1,2,4-oxadiazol-5-yl etc.), 1,2,4-triazolyl (e.g., 1,2,4-triazol-1-yl, 1,2,4-triazol-3-yl etc.), 1,2,3-triazolyl (e.g., 1,2,3-triazol-2-yl, 1,2,3-triazol-4-yl etc.), tetrazolyl (e.g., tetrazol-1-yl, tetrazol-5-yl etc.), benzimidazolyl (e.g., benzimidazol-1-yl, benzimidazol-2-yl etc.), indolyl(e.g., indol-1-yl, indol-3-yl etc.), 1H-indazolyl (e.g., 1H-indazol-1-yl etc.), 1H-pyrrolo[2,3-b]pyrazinyl (e.g., 1H-pyrrolo[2,3-b]pyrazin-1-yl etc.), 1H-pyrrolo[2,3-b]pyridyl (e.g., 1H-pyrrolo[2,3-b]pyridin-1-yl etc.), 1H-imidazo[4,5-b]pyridyl (e.g., 1H-imidazo[4,5-b]pyridin-1-yl etc.), 1H-imidazo[4,5-c]pyridyl (e.g., 1H-imidazo[4,5-c]pyridin-1-yl etc.), 1H-imidazo[4,5-b]pyrazinyl (e.g., 1H-imidazo[4,5-b]pyrazin-1-yl etc.) and the like; 5 to 7-membered non-aromatic heterocyclic groups such as pyrrolidinyl (e.g., 1-pyrrolidinyl etc.), piperidyl (e.g., 1-piperidyl etc.), morpholinyl (e.g., morpholin-4-yl etc.), thiomorpholinyl (e.g., thiomorpholin-4-yl etc.), piperazinyl (e.g., 1-piperazinyl etc.), hexametbyleneiminyl (e.g., hexamethylenimin-1-yl etc.), oxazolidinyl (e.g., oxazolidin-3-yl et.), thiazolidinyl (e.g., thiazolidin-3-yl, thiazolidin-2-yl etc.), imidazolidinyl (e.g., imidazolidin-3-yl etc.), imidazolinyl (e.g., imidazolin-1-yl, imidazolin-2-yl etc.), oxazolinyl (e.g., oxazolin-2-yl etc.), thiazolinyl (e.g., thiazolin-2-yl etc.), oxazinyl (e.g., oxazin-2-yl etc.) and the like, and the like. Of these, an aromatic heterocyclic group is preferable, and furyl, thienyl, pyridyl, quinolyl, isoquinolyl and the like are particularly preferably used.

The above-mentioned heterocyclic group may have the same or different, 1 to 5, preferably 1 to 3, substituent(s) at substitutable position(s). Examples of the substituent include (i) nitro group, (ii) cyano group, (iii) carboxyl group, (iv) $C_{1-6}$ alkoxy-carbonyl group (e.g., methoxycarbonyl, ethoxycarbonyl, tert-butoxycarbonyl and the like), (v) hydroxy group, (vi) halogen atom (e.g., fluorine, chlorine, bromine, iodine and the like), (vii) optionally halogenated $C_{1-6}$ alkyl group (e.g., methyl, ethyl, propyl, isopropyl, n-butyl, isobutyl, sec-butyl, tert-butyl, trifluoromethyl and the like), (viii) $C_{1-6}$ alkoxy group (e.g., methoxy, ethoxy, propoxy, isopropoxy, n-butoxy, isobutoxy, sec-butoxy, tert-butoxy and the like), (ix) benzyloxy group, (x) phenyl group, (xi) benzoyl group, (xii) phenoxy group, (xiii) amino group, (xiv) mono- or di-$C_{1-6}$ alkylamino group (e.g., methylamino, ethylamino, dimethylamino, diethylamino, methylethylamino and the like), (xv) $C_{1-6}$ alkyl-carbonyl group (e.g., methylcarbonyl, ethylcarbonyl, butylcarbonyl and the like), and the like.

The benzyloxy group, benzoyl group, phenyl group and phenoxy group as a substituent of the above-mentioned "hydrocarbon group" and "heterocyclic group" may have the same or different, 1 to 5, preferably 1 to 3, substituent(s) at substitutable position(s). Examples of the substituent include (i) $C_{1-3}$ alkylenedioxy group (e.g., methylenedioxy, ethylenedioxy and the like), (ii) nitro group, (iii) cyano group, (iv) hydroxy group, (v) halogen atom (e.g., fluorine, chlorine, bromine, iodine and the like), (vi) $C_{1-6}$ alkoxy group (e.g., methoxy, ethoxy, propoxy, isopropoxy, n-butoxy, isobutoxy, sec-butoxy, tert-butoxy and the like), (vii) $C_{1-6}$ alkyl group (e.g., methyl, ethyl, propyl, isopropyl, n-butyl, isobutyl, sec-butyl, tert-butyl and the like), (viii) benzyloxy group, (ix) amino group, (x) mono- or di-$C_{1-6}$ alkylamino group (e.g., methylamino, ethylamino, dimethylamino, diethylamino, methylethylamino and the like) and the like.

The above-mentioned electron-withdrawing group represented by $R^3$ is exemplified by —CN, —COOR$^7$ ($R^7$ is hydrogen atom or optionally substituted hydrocarbon group), —COR$^8$ ($R^8$ is hydrogen atom, optionally substituted hydrocarbon group or optionally substituted heterocyclic group) and the like, as well as optionally amidated carboxyl group, nitro group, a group represented by —(SO$_m$)R$^{15}$ (wherein m is 1 or 2 and $R^{15}$ is optionally substituted hydrocarbon group), a group represented by —PR$^{11}$R$^{12}$ (wherein $R^{11}$ and $R^{12}$ are each optionally substituted hydrocarbon group), a group represented by —(PO)(OR$^{13}$)(OR$^{14}$) wherein $R^{13}$ and $R^{14}$ are each hydrogen atom or optionally substituted hydrocarbon group) and the like. Of these, —CN, —COOR$^7$ ($R^7$ is hydrogen atom or optionally substituted hydrocarbon group), —COR$^8$ ($R^8$ is hydrogen atom, optionally substituted hydrocarbon group or optionally substituted heterocyclic group) and the like are preferable.

As the aforementioned "amidated carboxyl group" as an "electron-withdrawing group", there are exemplified a group represented by —(CO)NR$^{16}$R$^{17}$ wherein $R^{16}$ and $R^{17}$ are each hydrogen or optionally substituted hydrocarbon group, and $R^{16}$ and $R^{17}$ may be bonded with each other to form, together with the adjacent nitrogen atom, 5 to 7-membered, preferably 5 or 6-membered, cyclic amino (e.g., tetrahydropyrrole, piperazine, piperidine, morpholine, thiomorpholine and the like) and the like.

The aforementioned "optionally substituted hydrocarbon group" represented by $R^{11}$, $R^{12}$, $R_{13}$, $R^{14}$, $R^{15}$, $R^{16}$ or $R^{17}$ is exemplified by those exemplified as the aforementioned "optionally substituted hydrocarbon group" represented by $R^1$.

In the group represented by the formula —PR$^{11}$R$^{12}$ or —(PO)(OR$^{13}$)(OR$^{14}$) as the aforementioned "electron-withdrawing group", $R^{11}$ and $R^{12}$ or $R^{13}$ and $R^{14}$ may be bonded with each other to form, for example, lower ($C_{2-6}$) alkylene (e.g., dimethylene, trimethylene, tetramethylene and the like), lower ($C_{2-6}$)alkenylene (e.g., —CH$_2$—CH=CH—, —CH$_2$—CH$_2$—CH=CH—, —CH$_2$—CH=CH—CH$_2$— and the like) and the like, preferably lower ($C_{1-6}$)alkylene, more preferably lower ($C_{2-4}$)alkylene. These divalent groups may have substituent(s), where examples of the substituent include hydroxyl group, halogen, $C_{1-4}$ alkyl, $C_{1-4}$ alkoxy and the like.

In the above-mentioned formulas, $R^1$ and $R^2$ are preferably hydrogen atom, optionally substituted alkyl group, optionally substituted aralkyl group, optionally substituted aryl group, optionally substituted heterocyclic group and the like. Particularly, $R^1$ is preferably optionally substituted aryl group or optionally substituted aromatic heterocyclic group, particularly, $R^1$ is preferably optionally substituted phenyl group. $R^1$ is more preferably phenyl group optionally having 1 to 3 substituent(s) selected from halogen atom (preferably chlorine), optionally halogenated $C_{1-6}$ alkyl group (preferably trifluoromethyl) or $C_{1-6}$ alkoxy group (preferably methoxy). Particularly preferably, $R^1$ is phenyl group optionally substituted by 1 to 3 halogen atom(s) (preferably chlorine). As $R^2$, hydrogen atom is preferable.

In the above-mentioned formulas, $R^4$, $R^5$ and $R^6$ are preferably hydrogen atom, optionally substituted alkyl group (preferably $C_{1-6}$ alkyl group such as methyl and the like), optionally substituted aryl group (preferably phenyl) and the like, particularly preferably hydrogen atom.

In the above-mentioned formulas, $R^3$ is preferably —CN, —COOR$^7$ ($R^7$ is hydrogen atom or optionally substituted alkyl group) or —COR$^8$ ($R^8$ is hydrogen atom, optionally substituted alkyl group or optionally substituted aryl group), particularly —COOR$^7$ ($R^7$ is hydrogen atom or optionally substituted alkyl group).

As used herein, $R^7$ and $R^8$ are particularly preferably $C_{1-6}$ alkyl group such as methyl and the like.

With regard to the above-mentioned "optionally substituted amino group" represented by $R^{18}$, the if substituent is exemplified by the aforementioned "optionally substituted hydrocarbon group" exemplified as $R^1$ and the like. $R^{18}$ is preferably amino group optionally mono- or di-substituted by substituent(s) selected from $C_{1-6}$ alkyl group and $C_{6-14}$ aryl-$C_{1-6}$ alkyl group. $R^{18}$ is more preferably amino group.

In the present invention, the aforementioned compound represented by the formula (I) or a salt thereof [hereinafter sometimes to be referred to as compound (I)] is reacted with the aforementioned compound represented by the formula (II) or a salt thereof [hereinafter sometimes to be referred to as compound (II)], in the presence of an acid or a base to produce a compound represented by the aforementioned formula (III) or a salt thereof [hereinafter sometimes to be referred to as compound (III)].

In the present specification, compound (II) and compound (III), wherein $R^3$ is —COOR$^7$ ($R^7$ is as defined above), may be described as compound (IIa) and compound (IIIa), respectively.

Examples of the acid to be used in this reaction include mineral acids (e.g., hydrochloric acid, hydrobromic acid, sulfuric acid, phosphoric acid etc.), organic acids (e.g., acetic acid, propionic acid, butyric acid, methanesulfonic acid, ethanesulfonic acid, benzenesulfonic acid, toluenesulfonic acid, camphorsulfonic acid etc.), Lewis acids (e.g., aluminum chloride, tin chloride, iron chloride, titanium chloride (titanium tetrachloride), boron trifluoride, boron trichloride etc.), strong acid resin (e.g., Dowex 50, Amberlite IR120 etc.), polyphosphoric acid, polyphosphoric acid ester and the like. The acid is preferably sulfuric acid, methanesulfonic acid or boron trifluoride. Of these, mineral acids are preferable, particularly, sulfuric acid is preferable.

Examples of the base to be used in this reaction include alkali metal alkoxides (e.g., sodium methoxide, sodium ethoxide, sodium-tert-butoxide, potassium-tert-butoxide etc.), tertiary amines (e.g., trimethylamine, triethylamine, tributylamine, diisopropylethylamine, 1,8-diazabicyclo[5.4.0]undec-7-ene(DBU), 1,5-diazabicyclo[4.3.0]non-5-ene(DBN) etc.), aromatic amines (e.g., pyridine, picoline, quinoline, dimethylaniline, diethylaniline etc.), strong base resins (e.g., Dowex 1, Amberlite IRA400, BioRad AGI etc.) and the like. The base is preferably alkali metal alkoxides or tertiary amines, particularly preferably sodium methoxide or triethylamine.

This reaction is generally carried out in a solvent. Examples of the solvent include halogenated hydrocarbons (e.g., dichloromethane, chloroform, 1,2-dichloroethane, 1,1,2,2-tetrachloroethane etc.), aromatic hydrocarbons (e.g., benzene, toluene, xylene, chlorobenzene, nitrobenzene etc.), ethers (e.g., ethyl ether, isopropyl ether, tetrahydrofuran, dioxane and the like), nitriles (e.g., acetonitrile, propionitrile and the like), esters (methyl acetate, ethyl acetate etc.), alcohols (e.g., methanol, ethanol, propanol, isopropanol, butanol, methoxyethanol etc.) and the like. These solvents may be used in a combination of two or more kinds thereof at an appropriate mixing ratio. Alternatively, the aforementioned acid or base may be used as a solvent. The solvent is preferably nitrile, alcohol, aromatic hydrocarbon, more preferably, acetonitrile, methanol or toluene. Particularly, acetonitrile is preferable.

The amount of compound (II) to be used is generally 1–20 equivalent(s), preferably 1–5 equivalent(s), relative to compound (I). The amount of the acid or base to be used is generally 0.01–30 equivalent(s), preferably 0.05–10 equivalents), relative to compound (I).

The reaction of compound (I) and compound (II) is preferably carried out in the presence of an acid, wherein the amount of the acid to be used is generally 0.1–30 equivalent (s), preferably 0.5–10 equivalent(s), relative to compound (I).

The reaction temperature is generally −30° C. to 150° C., preferably −10° C. to 100° C.

The reaction time is generally 0.5 hour to 24 hours, preferably 1 hour to 10 hours.

The compound (III) thus obtained can be easily isolated by a known method, such as concentration, changing of liquid properties, solvent extraction, crystallization and the like. Recrystallization affords a compound having a higher purity.

In the production method of the present invention, compound (I) as a starting material can be produced, for example, according to the following method.

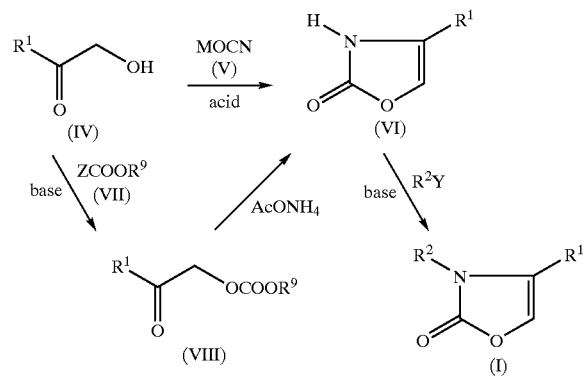

wherein M is an alkali metal such as sodium, potassium and the like, Z is a halogen atom (e.g., chlorine, bromine and the like), Y is a halogen atom (e.g., chlorine, bromine and the like) or —OSO$_2$R$^{10}$ (R$^{10}$ is an optionally substituted alkyl group or an optionally substituted aryl group), Ac is an acetyl group, R$^9$ is an alkyl group, aralkyl group or aryl group, and other symbols are as defined above.

In the above-mentioned formula, examples of the "alkyl group" represented by R$^9$ include the aforementioned "alkyl group (preferably alkyl group having 1 to 6 carbon atom(s))" exemplified for R$^1$.

In the above-mentioned formula, examples of the "aralkyl group" represented by R$^9$ include the aforementioned "aralkyl group (preferably $C_{6-14}$ aryl-$C_{1-6}$ alkyl group)" exemplified for R$^1$.

In the above-mentioned formula, examples of the "aryl group" represented by R$^9$ include the aforementioned "aryl group (preferably aryl group having 6 to 14 carbon atoms)" exemplified for R$^1$.

In the above-mentioned formula, examples of the "alkyl group" of the "optionally substituted alkyl group" represented by $R^{10}$ include the aforementioned "alkyl group (preferably alkyl group having 1 to 6 carbon atom(s))" exemplified for $R^1$. The "alkyl group" may have the same or different, 1 to 5, preferably 1 to 3, substituent(s) at substitutable position(s) Examples of such substituent include those similar to the substituent of the aforementioned "aliphatic hydrocarbon group" exemplified for $R^1$.

In the above-mentioned formula, the "aryl group" of the "optionally substituted aryl group" represented by $R^{10}$ includes the aforementioned "aryl group (preferably aryl group having 6 to 14 carbon atoms)" exemplified for $R^1$. The "aryl group" may have the same or different, 1 to 5, preferably 1 to 3, substituent(s) at substitutable position(s). Examples of such substituent include those similar to the substituent of the aforementioned "aryl group" exemplified as $R^1$.

$R^{10}$ is particularly preferably $C_{1-6}$ alkyl group (preferably methyl); a phenyl group optionally substituted by 1 to 3 $C_{1-6}$ alkyl group(s) (preferably methyl).

First, compound (IV) and compound (V) are reacted in the presence of an acid to give compound (VI). This reaction is generally carried out in a solvent. Examples of the solvent include alcohols (e.g., methanol, ethanol, propanol, isopropanol, butanol, methoxyethanol and the like), halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), nitriles (e.g., acetonitrile, propionitrile and the like), esters (methyl acetate, ethyl acetate and the like) and the like. These solvents may be used in a combination of two or more kinds thereof at an appropriate mixing ratio. The solvent is particularly preferably alcohol such as isopropanol and the like.

As the acid, for example, organic acids (e.g., acetic acid, propionic acid, butyric acid, methanesulfonic acid, ethanesulfonic acid, benzenesulfonic acid, toluenesulfonic acid, camphorsulfonic acid and the like), mineral acids (e.g., hydrochloric acid, hydrobromic acid, sulfuric acid, phosphoric acid and the like) and the like are used. Of these, organic acids are preferable, and acetic acid is particularly preferable.

The amount of compound (V) to be used is generally 1–10 equivalent(s), preferably 1–5 equivalents), relative to compound (IV). The amount of acid to be used is generally 1–30 equivalent(s), preferably 1–10 equivalents), relative to compound (V).

The reaction temperature is generally –10° C. to 120° C., preferably –5° C. to 90° C.

The reaction time is generally 0.5 hour to 72 hours, preferably 1 hour to 36 hours.

The compound (VI) can be also produced by reacting compound (IV) with compound (VII) in the presence of a base to give compound (VIII), and reacting the compound (VIII) with ammonium acetate.

The reaction of compound (IV) and compound (VII) is generally carried out in a solvent in the presence of a base. This solvent may be any as long as it does not inhibit the reaction and is exemplified by halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), nitrites (e.g., acetonitrile, propionitrile and the like), esters (methyl acetate, ethyl acetate and the like), dimethylformamide, dimethylacetamide, dimethyl sulfoxide and the like. These solvents may be used in a combination of two or more kinds thereof at an appropriate mixing ratio.

As the base, for example, tertiary amines (e.g., trimethylamine, triethylamine, tributylamine, N-ethyldiisopropylamine, N-methylmorpholine and the like), aromatic amines (e.g., pyridine, picoline, quinoline and the like), alkali metal carbonate (e.g., sodium hydrogencarbonate, potassium carbonate, sodium carbonate, cesium carbonate and the like), alkali metal hydroxide (e.g., potassium hydroxide, sodium hydroxide, calcium hydroxide and the like) and the like are used.

Each amount of compound (VII) and a base to be used is generally 1–5 equivalent(s), preferably 1–3 equivalent(s), relative to compound (IV).

The reaction temperature is generally –30° C. to 100° C., preferably –15° C. to 60° C.

The reaction time is generally 15 minutes to 24 hours, preferably 0.5 hour to 12 hours.

The thus-obtained compound (VIII), after isolation by a known method or as its reaction mixture, is reacted with ammonium acetate to give compound (VI). This reaction is carried out in a solvent. This solvent may be any as long as it does not inhibit the reaction and is exemplified by halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), nitrites (e.g., acetonitrile, propionitrile and the like), esters (methyl acetate, ethyl acetate and the like), dimethylformamide, dimethylacetamide, dimethyl sulfoxide and the like. These solvents may be used in a combination of two or more kinds thereof at an appropriate mixing ratio. A weak acid may be used as a solvent. The weak acid to be used includes, for example, formic acid, acetic acid, propionic acid and the like. A mixed solvent of these weak acids and the above-mentioned solvents may be used for the reaction.

The amount of ammonium acetate to be used is generally 1–20 equivalents), preferably 1–10 equivalent(s), relative to compound (VIII).

The reaction temperature is generally –10° C. to 150° C., preferably 0° C. to 120° C.

The reaction time is generally 15 minutes to 24 hours, preferably 0.5 hour to 12 hours.

The thus-obtained compound (VI), after isolation by a known method or as its reaction mixture, is used as the starting material for the production method of the present invention, as well as the starting material for producing compound (I) by N-alkylation in the presence of a base. The conditions of the N-alkylation reaction may be those under which compound (VIII) is produced or similar method. As the base, those exemplified for the reaction below of the compound (IV) with cyanamide compound are used.

According to the present invention, the aforementioned compound represented by the formula (IX) or a salt thereof [hereinafter sometimes to be referred to as compound (IX)] and compound (II) are reacted in the presence of an acid to give a compound represented by the aforementioned formula (X) or a salt thereof [hereinafter sometimes to be referred to as compound (X)].

In the present specification, compound (X) wherein $R^3$ is —COOR$^7$ ($R^7$ is as defined above) may be referred to as compound (Xa).

As the acid to be used for this reaction, those exemplified for the aforementioned reaction of compound (I) and compound (II) are mentioned. Of these, Lewis acids are preferable, particularly titanium chloride is preferable.

This reaction is generally carried out in a solvent. Examples of the solvent include those exemplified for the aforementioned reaction of compound (I) and compound (II). In some cases, the acid to be used may be used as a solvent. The solvent is preferably halogenated hydrocarbon, particularly preferably dichloromethane.

The amount of compound (II) to be used is generally 1–20 equivalent(s), preferably 1–5 equivalents), relative to compound (IX). The amount of the acid to be used is generally 0.1–30 equivalents), preferably 0.5–10 equivalent(s), relative to compound (IX).

The reaction temperature and reaction time are the same as those for the aforementioned reaction of compound (I) and compound (II).

The compound (X) thus obtained can be easily isolated by a known method such as concentration, changing of liquid properties, solvent extraction, crystallization and the like. Recrystallization affords a compound having a higher purity.

The compound (IX) to be used as a starting material in the above-mentioned production method can be produced, for example, by reacting compound (IV) with a cyanamide compound represented by the formula: $R^{18}CN$ [the symbol in the formula is as defined above] in the presence of a base.

As the base, for example, tertiary amines (e.g., trimethylamine, triethylamine, tributylamine, N-ethyldiisopropylamine, N-methylmorpholine and the like), aromatic amines (e.g., pyridine, picoline, quinoline, isoquinoline, N,N-dimethylaniline, N,N-diethylaniline and the like), alkali metal carbonates (e.g., sodium hydrogencarbonate, potassium carbonate, sodium carbonate, cesium carbonate and the like), alkali metal hydroxides (e.g., potassium hydroxide, sodium hydroxide, calcium hydroxide and the like), alkali metal alkoxides (e.g., potassium tert-butoxide, sodium methoxide, sodium ethoxide, sodium n-butoxide, sodium tert-butoxide and the like) and the like are used. Particularly, alkali metal alkoxide is preferable.

This reaction is generally carried out in a solvent. This solvent may be any as long as it does not inhibit the reaction and is exemplified by alcohols (e.g., methanol, ethanol, propanol, isopropanol, butanol, methoxyethanol and the like), halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene, benzotrifluoride and the like), ethers (e.g. ethyl ether, isopropyl ether, tetrahydrofuran, dioxane and the like), nitriles (e.g., acetonitrile, propionitrile and the like), esters (methyl acetate, ethyl acetate and the like) and the like. These solvents may be used in a combination of two or more kinds thereof at an appropriate mixing ratio. The solvent is preferably alcohol.

The amount of the cyanamide compound to be used is generally 1–10 equivalent(s), preferably 1–5 equivalents), relative to compound (IV).

The amount of the base to be used is generally 0.01–10 equivalents), preferably 0.1–5 equivalents), relative to compound (IV).

The reaction temperature is generally −50° C. to 150° C., preferably −20° C. to 120° C.

The reaction time is generally 15 minutes to 24 hours, preferably 0.5 hour to 12 hours.

The thus-obtained compound (IX), after isolation by a known method or as its reaction mixture, is used as the starting material for the next step.

When compound (I), compound (II), compound (III), compound (IX), compound (X); and each starting material compound used for the production step of compound (I) or compound (IX) are basic compounds depending on the kind of the substituent exemplified above, they may form a salt with an acid. This acid may be any as long as it does not inhibit the reaction and is exemplified by inorganic acids such as hydrochloric acid, hydrobromic acid, phosphoric acid, sulfuric acid, nitric acid, sulfamic acid and the like; organic acids such as formic acid, acetic acid, trifluoroacetic acid, tartaric acid, citric acid, fumaric acid, maleic acid, succinic acid, malic acid, p-toluenesulfonic acid, methanesulfonic acid, benzenesulfonic acid and the like; acidic amino acids such as aspartic acid, glutamic acid and the like; and the like. When the obtained compound is a salt, it may be converted to a free base by a conventional method.

When compound (I), compound (II), compound (III), compound (IX), compound (X); and each starting material compound used for the production step of compound (I) or compound (IX) are acidic compounds depending on the kind of the substituent exemplified above, they may form a salt with a base. This salt with a base may be any as long as it does not inhibit the reaction and is exemplified by salt with inorganic base, salt with organic base, salt with basic amino acid and the like. Preferable examples of the salt with inorganic base include alkali metal salts such as sodium salt, potassium salt and the like; alkaline earth metal salts such as calcium salt, magnesium salt and the like; aluminum salt, ammonium salt and the like. Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like. Preferable examples of the salt with basic amino acid include salts with arginine, lysin, ornithine and the like. When the obtained compound is a salt, it may be converted to a free acid by a conventional method.

The compound (III) and compound (X) obtained by the production method of the present invention are useful as a synthetic intermediate for a pharmaceutical product such as an agent for treating diabetes as described in, for example, JP-A-9-323983 (WO97/36882) and the like, and the like. For example, the oxazole derivative described in JP-A-9-323983 can be produced using compound (III) or compound (X) as a starting material and according to the method to be mentioned below or the method described in JP-A-9-323983 or a similar method.

For example, by subjecting compound (III) or compound (X) to a halogenation reaction, a compound represented by the formula

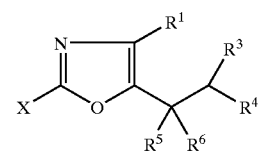

(XI)

wherein X is a halogen atom, and other symbols are as defined above, or a salt thereof, can be produced.

The halogen atom represented by X is exemplified by fluorine, chlorine, bromine and the like.

The halogenation reaction of compound (III) is generally carried out in a solvent that does not exert an adverse influence on the reaction, in the presence of a halogenating agent. Alternatively, an excess halogenating agent may be used as a solvent.

The halogenating agent is exemplified by phosphorus oxychloride, phosphorus trichloride, phosphorus pentachloride, thionyl chloride, phosphorus tribromide and the like. Of these, phosphorus oxychloride is preferable.

The amount of the halogenating agent to be used is generally 1–50 equivalents), preferably 3–20 equivalents, relative to compound (III).

As the solvent that does not exert an adverse influence on the reaction, for example, halogenated hydrocarbons (e.g., dichloromethane, chloroform, 1,2-dichloroethane, 1,1,2,2-tetrachloroethane and the like), ethers (e.g., ethyl ether, isopropyl ether, tetrahydrofuran, dioxane and the like), nitriles (e.g., acetonitrile, propionitrile and the like), esters (methyl acetate, ethyl acetate and the like), aromatic hydrocarbons (e.g., benzene, toluene, xylene, chlorobenzene, nitrobenzene, benzotrifluoride and the like), pyridine and the like are used. These solvents may be used in a combination of two or more kinds thereof at an appropriate mixing ratio. The solvent is preferably pyridine.

The reaction temperature is generally 20° C. to 180° C., preferably 50° C.–130° C.

The reaction time is generally 30 minutes to 20 hours.

The compound (X) is halogenated by, for example, conducting a Sandmeyer reaction known per se, namely substitution of diazo group for halogen after diazotization reaction.

The diazotization reaction is generally carried out using a diazotizing agent. As the diazotizing agent, for example, nitrites (e.g., nitrous acid, sodium nitrite and the like), alkyl nitrites (e.g., ethyl nitrite, butyl nitrite, amyl nitrite, isoamyl nitrite and the like) and the like are used. In addition, nitrosyl halide such as nitrosyl chloride and the like can be mentioned. The amount of the diazotizing agent to be used is generally about 1–10 molar equivalent(s) relative to compound (X). The diazotizing agent is preferably nitrite such as sodium nitrite and the like.

The substitution of diazo group for halogen is, for example, carried out in a solvent that does not exert an adverse influence on the reaction, in the presence of (i) copper halide, or (ii) hydrochloric acid or hydrobromic acid and copper powder or copper salt.

The copper halide to be used includes, for example, copper(I) chloride, copper(I) bromide, copper(I) iodide, copper(II) chloride, copper(II) bromide, copper(II) iodide and the like. The copper salt to be used includes, for example, copper sulfate, copper carbonate, copper oxide and the like. The amount of the copper halide, copper powder or copper salt to be used is generally about 0.001–20 molar equivalent(s) relative to compound (X).

As the solvent that does not exert an adverse influence on the reaction, for example, alcohols (e.g., methanol, ethanol, propanol, isopropanol, butanol, methoxyethanol and the like), ethers (e.g., ethyl ether, isopropyl ether, tetrahydrofuran, dioxane and the like), acetone, dimethyl sulfoxide, phosphoric acid, acetic acid, water and the like are mentioned. These solvents may be used in a combination of two or more kinds thereof at an appropriate mixing ratio.

The reaction temperature is generally about −50° C. to 200° C., preferably about −20° C. to 150° C.

The reaction time is generally 30 minutes to 20 hours.

The compound (XI) thus obtained can be easily isolated by a known method such as concentration, changing of liquid properties, solvent extraction, crystallization and the like. Recrystallization affords a compound having a higher purity.

In the present specification, compound (XI) wherein $R^3$ is —$COOR^7$ ($R^7$ is as defined above) may be sometimes referred to as compound (XIa).

The compound (XVIII) useful as an agent for the prophylaxis or treatment of diabetes or diabetic complications (e.g., nephropathy, retinopathy, neuropathy and the like) can be produced by, for example, subjecting compound (XIa) to the following reaction.

The compound (XVIII), as such or after mixing with a pharmacologically acceptable carrier known per se and the like and forming into a preparation such as tablets, capsules, injections and the like, can be safely administered to a mammal (e.g., human, mouse, rat, a rabbit, dog, cat, bovine, horse, pig, monkey and the like).

While the dose of compound (XVIII) varies depending on the subject of administration, administration route and the like, for example, it is generally about 0.05–500 mg/kg body weight, preferably about 5–100 mg/kg body weight, for each oral administration to adult patients with diabetes, wherein the dose is preferably given once to 3 times a day.

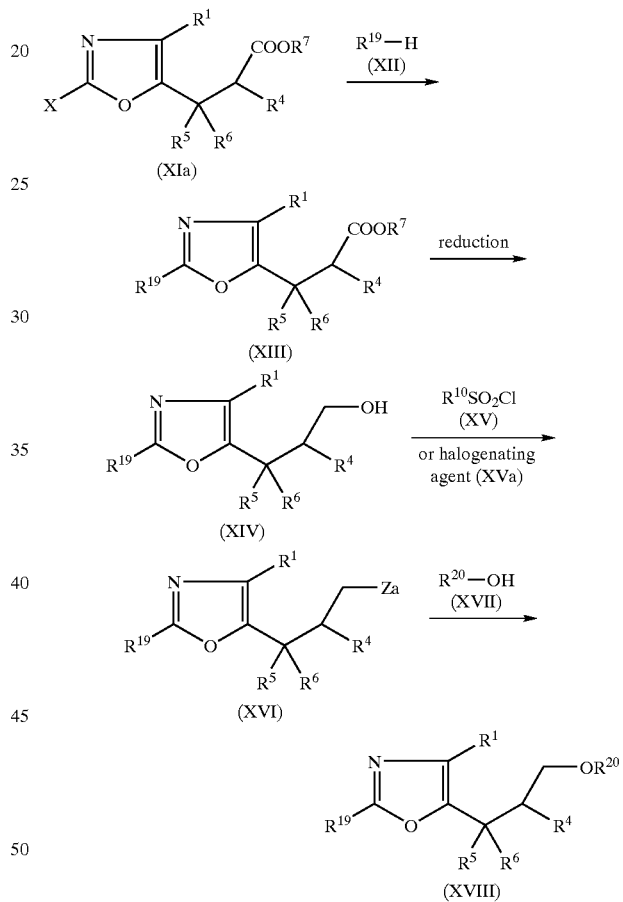

wherein $R^{19}$ is an optionally substituted heterocyclic group containing nitrogen, which is bonded via a nitrogen atom, $R^{20}$ is an optionally substituted hydrocarbon group, Za is a halogen atom (e.g., chlorine, bromine and the like) or —$OSO_2R^{10}$ ($R^{10}$ is as defined above), and other symbols are as defined above.

With regard to the "optionally substituted heterocyclic group containing nitrogen, which is bonded via a nitrogen atom" represented by $R^{19}$, the "heterocyclic group containing nitrogen, which is bonded via a nitrogen atom" is exemplified by a 5 to 10-membered aromatic heterocyclic group containing nitrogen such as 1-pyrrolyl, 1-imidazolyl, 1-pyrazolyl, 1,2,4-triazol-1-yl, 1,2,4-triazol-4-yl, 1,2,3-triazol-1-yl, 1,2,3-triazol-2-yl, tetrazol-1-yl, tetrazol-2-yl, benzimidazol-1-yl, indol-1-yl, 1H-indazol-1-yl, 1H-pyrrolo[2,3-b]pyrazin-1-yl, 1H-pyrrolo[2,3-b]pyridin-1-yl, 1H-imidazo[4,5-b]pyridin-1-yl, 1H-imidazo[4,5-c]pyridin-1-yl, 1H-imidazo[4,5-b]pyrazin-1-yl and the like; a 5 to 7-membered non-aromatic heterocyclic group containing nitrogen such as 1-pyrrolidinyl, 1-piperidyl, morpholin-4-yl, thiomorpholin-4-yl, 1-piperazinyl, hexamethyleneimin-1-yl, oxazolidin-3-yl, thiazolidin-3-yl, imidazolidin-1-yl, imidazolin-1-yl, oxazolin-3-yl, thiazolin-3-yl, oxazin-4-yl and the like; and the like. It is preferably an aromatic heterocyclic group containing nitrogen, and particularly preferably 1-imidazolyl, 1-pyrazolyl, 1,2,4-triazol-1-yl, 1,2,4-triazol-4-yl, benzimidazol-1-yl and the like.

The above-mentioned "heterocyclic group containing nitrogen, which is bonded via a nitrogen atom" may have the same or different, 1 to 5, preferably 1 to 3, substituent(s) at substitutable position(s). Examples of the substituent include the substituent of the aforementioned "optionally substituted heterocyclic group" exemplified as $R^1$. $R^{19}$ is particularly preferably 1-imidazolyl group optionally substituted by 1 to 3 $C_{1-6}$ alkyl group(s).

Examples of the "optionally substituted hydrocarbon group" represented by $R^{20}$ include the aforementioned "optionally substituted heterocyclic group" exemplified as $R^1$ and the like. $R^{20}$ is particularly preferably $C_{6-14}$ aryl group (preferably phenyl) optionally substituted by 1 to 3 $C_{1-6}$ alkyl group(s).

First, compound (XIa) and compound (XII) are reacted to give compound (XIII).

This reaction is generally carried out in a solvent that does not exert an adverse influence on the reaction, in the presence of a base.

As the base, those used for the aforementioned reaction of compound (IV) and cyanamide compound are mentioned. Alternatively, compound (XII) itself may be used as a base by using an excess compound (XII).

As the solvent that does not exert an adverse influence on the reaction, for example, ethers (e.g., ethyl ether, isopropyl ether, tetrahydrofuran, dioxane and the like), aromatic hydrocarbons (e.g., benzene, toluene, xylene, chlorobenzene, nitrobenzene, benzotrifluoride and the like), N,N-dimethylformamide, dimethyl sulfoxide, acetone, N-methylpyrrolidone and the like are mentioned. These solvents may be used in a combination of two or more kinds thereof at an appropriate mixing ratio. The solvent is particularly preferably dimethyl sulfoxide.

The amount of compound (XII) to be used is generally 1–20 equivalent(s), preferably 1–5 equivalent(s), relative to compound (XIa).

The amount of the base to be used is generally 0.01–10 equivalent(s), preferably 0.1–5 equivalent(s), relative to compound (XIa).

The reaction temperature is generally 20° C. to 180° C., preferably 80° C. to 140° C.

The reaction time is generally 15 minutes to 20 hours.

Then, compound (XIII) is subjected to reduction reaction to give compound (XIV).

This reaction is generally carried out in a solvent that does not exert an adverse influence on the reaction, in the presence of a reducing agent.

As the reducing agent, for example, metal hydrides such as alkali metal borohydride (e.g., sodium borohydride, lithium borohydride and the like) and the like; metal hydrogen complex compounds such as lithium aluminum hydride, sodium dihydro-bis(2-methoxyethoxy)aluminate and the like; organic tin compounds such as triphenyltin hydride and the like; diborane, substituted borane and the like are used.

Of these, metal hydrogen complex compounds such as sodium dihydro-bis(2-methoxyethoxy)aluminate and the like are preferable.

As the solvent that does not exert an adverse influence on the reaction, for example, alcohols (e.g., methanol, ethanol, propanol, isopropanol, butanol, methoxyethanol and the like), halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), N,N-dimethylformamide and the like are used. These solvents may be used in a combination of two or more kinds thereof at an appropriate mixing ratio. The solvent is preferably aromatic hydrocarbons, particularly preferably toluene.

The reaction temperature is generally −20° C. to 150° C., preferably 0° C. to 100° C.

The reaction time is generally 5 minutes to 10 hours.

Then, compound (XIV) is reacted with compound (XV) or halogenating agent (XVa) to give compound (XVI).

Preferable examples of compound (XV) include methanesulfonyl chloride (mesyl chloride), toluenesulfonyl chloride (tosyl chloride), benzenesulfonyl chloride and the like. Preferable examples of halogenating agent (XVa) include thionyl chloride, thionyl bromide, phosphorus trichloride, phosphorus tribromide, phosphorus oxychloride, phosphorus pentachloride and the like.

This reaction is generally carried out in a solvent that does not exert an adverse influence on the reaction, in the presence of a base.

As the base, for example, tertiary amines (e.g., trimethylamine, triethylamine, tributylamine, N-ethyldiisopropylamine, N-methylmorpholine and the like), aromatic amines (e.g., pyridine, picoline, quinoline, isoquinoline, N,N-dimethylaniline, N,N-diethylaniline and the like), alkali metal carbonates (e.g., sodium hydrogencarbonate, potassium carbonate, sodium carbonate, cesium carbonate and the like) and the like are used. Of these, tertiary amines such as triethylamine, N-ethyldiisopropylamine and the like are preferable.

As the solvent that does not exert an adverse influence on the reaction, for example, halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), esters (methyl acetate,, ethyl acetate and the like) and the like are used. These solvents may be used in a combination of two or more kinds thereof at an appropriate mixing ratio. The solvent is preferably aromatic hydrocarbons or ethers, particularly preferably toluene or tetrahydrofuran.

The amount of compound (XV) or halogenating agent (XVa) to be used is generally 1–5 equivalent(s) relative to compound (XIV).

The amount of the base to be used is generally 0.01–10 equivalent(s), preferably 0.1–5 equivalent(s), relative to compound (XIV).

The reaction temperature is generally −20° C. to 150° C., preferably 0° C. to 100° C.

The reaction time is generally 5 minutes to 20 hours.

Furthermore, compound (XVI) and compound (XVII) are reacted to give compound (XVIII).

This reaction is generally carried out in a solvent that does not exert an adverse influence on the reaction, in the presence of a base.

As the solvent that does not exert an adverse influence on the reaction, for example, halogenated hydrocarbons (e.g., dichloromethane, chloroform, 1,2-dichloroethane, 1,1,2,2-tetrachloroethane and the like), aromatic hydrocarbons (e.g., benzene, toluene, xylene, chlorobenzene, nitrobenzene and the like), ethers (e.g., ethyl ether, isopropyl ether, tetrahydrofuran, dioxane and the like), dimethylformamide, dimethylacetamide, dimethyl sulfoxide and the like are mentioned. These solvents may be used in a combination of two or more kinds thereof at an appropriate mixing ratio. The solvent is preferably aromatic hydrocarbons or ethers, particularly preferably toluene or tetrahydrofuran.

As the base, those used for the aforementioned reaction of compound (XIa) and compound (XII) are mentioned.

The amount of each of compound (XVII) and base to be used is generally 1–10 equivalents), preferably 1–5 equivalent(s), relative to compound (XVI).

The reaction temperature is generally −50° C. to 150° C., preferably −10° C. to 120° C.

The reaction time is generally 30 minutes to 20 hours.

In this reaction, the use of a phase-transfer catalyst (PTC) is preferable for promoting the reaction. As the phase-transfer catalyst, for example, tetraethylammonium chloride, tetrabutylamimonium chloride, tetrabutylammonium bromide, benzyltriethylammonium chloride, cetylbenzyldimethylammonium chloride and the like are mentioned. Of these, tetrabutylammonium bromide is preferable.

The amount of the phase-transfer catalyst to be used is, for example, generally 0.001–5 equivalent(s) relative to compound (XVI).

The compound (XVIII) can be also produced by subjecting compound (XIV) and compound (XVII) to Mitsunobu reaction known per se.

This reaction is generally carried out in a solvent that does not exert an adverse influence on the reaction, in the presence of an organic phosphorus compound and an electrophile.

As the solvent that does not exert an adverse influence on the reaction, for example, the solvents that do not exert an adverse influence, which are used for the aforementioned reaction of compound (XVI) and compound (XVII), are mentioned.

As the organic phosphorus compound, for example, triphenylphosphine, tributylphosphine and the like are mentioned.

As the electrophile, for example, diethyl azodicarboxylate, diisopropyl azodicarboxylate, azodicarbonyl dipiperazine and the like are mentioned.

The amount of each of the organic phosphorus compound and electrophile to be used is, for example, generally 1–5 equivalents relative to compound (XIV).

The reaction temperature is generally −50° C. to 150° C., preferably −10° C. to 120° C.

The reaction time is generally 30 minutes to 20 hours.

The aforementioned compounds (XIII), (XIV), (XVI) and (XVIII) can be easily isolated by a known method such as concentration, changing of liquid properties, solvent extraction, crystallization and the like. Recrystallization affords a compound having a higher purity. The compounds (XIII), (XIV) and (XVI) may be used for the next reaction without isolation.

Each starting material compound used for the aforementioned production step of compound (XI) and compound (XVIII) may form a salt with an acid or base in the same manner as with the aforementioned compound (I) and the like.

BEST MODE FOR EMBODIMENT OF THE INVENTION

The present invention is explained in more detail in the following by way of Examples and Reference Examples. It is needless to say that the present invention is not limited by these examples.

EXAMPLES

Example 1

Methyl 2-(4-(4-chlorophenyl)-2-oxo-4-oxazolin-5-yl)propionate

To a solution of 4-(4-chlorophenyl)-2-oxo-4-oxazoline (794.3 g) in acetonitrile (2383 mL) was added dropwise conc. sulfuric acid (1195 g) under ice-cooling at not higher than 10° C. Then methyl acrylate (731 mL) was added at not higher than 10° C., and the mixture was taken out from an ice-bath and stirred at room temperature for 3 h. Water (7.94 L) was added under ice-cooling at not higher than 20° C. The precipitated crystals were collected by filtration and washed successively with 1% aqueous sodium hydrogencarbonate, water, isopropyl ether to give methyl 2-(4-(4-chlorophenyl)-2-oxo-4-oxazolin-5-yl)propionate (1017.8 g; yield 89%). Recrystallization from methanol gave colorless crystals.

Elemental analysis value for $C_{13}H_{12}ClNO_4$

Calculated: C, 55.43; H, 4.29; N, 4.97. Found: C, 55.23; H, 3.99; N, 5.08.

NMR(CDCl$_3$): 2.70(2H, t, J=7.0 Hz), 2.98(2H, t, J=7.0 Hz), 3.65(3H, s), 7.42(5H, s), 10.37(1H, s)

Example 2

4-(4-Phenyl-2-oxo-4-oxazolin-5-yl)-4-phenyl-2-butanone

To a solution of 4-phenyl-2-oxo-4-oxazoline (1.61 g) and benzalacetone (1.46 g) in acetonitrile (20 ml) was added dropwise methanesulfonic acid (0.96 g). After stirring the obtained mixture at room temperature for 30 min, water was added, and the mixture was extracted with ethyl acetate. The extract was washed with water and dried (MgSO$_4$), and the solvent was evaporated. The residue was subjected to silica gel column chromatography and eluted with hexane-ethyl acetate (1:1). The solvent was evaporated. Crystallization from isopropyl ether gave 4-(4-phenyl-2-oxo-4-oxazolin-5-yl)-4-phenyl-2-butanone (2.65 g; yield 86.3%). Recrystallization from ethanol gave colorless crystals.

Elemental analysis value for $C_{19}H_{17}NO_3$

Calculated: C, 74.25; H, 5.58; N, 4.56. Found: C, 74.28; H, 5.72; N, 4.52.

NMR(CDCl$_3$): 2.16(3H, s), 3.02(1H, dd, J=17.7 and 6.0 Hz), 3.34(1H, dd, J=17.7 and 8.4 Hz), 4.67(1H, dd, J=8.4 and 6.0 Hz), 7.21–7.50(10H, m), 10.10(1H, s)

Example 3

Methyl 2-(4-(4-chlorophenyl)-2-oxo-4-oxazolin-5-yl)propionate 4-(4-Chlorophenyl)-2-oxo-4-oxazoline (3.00 g) and methyl acrytate (1.52 mL) were dissolved in methanol (15 mL), and a solution (0.30 mL) of 28% sodium methoxide (NaOMe) in methanol was added. The obtained mixture was stirred with reflux for 2 h, and the solvent was concentrated under reduced pressure. Toluene (21 mL) and water (21 mL) were added to the residue and the mixture was stirred at room temperature for 1 h. The mixture was cooled to not higher than 5° C. and, after stirring for 1 h, the precipitated crystals were collected by filtration, and washed successively with water (21 mL) and isopropyl ether (21 mL). The crystals were dried under reduced pressure at 50° C. to give the title compound (2.85 g; yield 66.0%) as pale-purple crystals. The NMR data of the product was identified well with the data of the compound obtained in Example 1.

Example 4

5-(3-oxo-1-phenylbutyl)-4-phenyl-2-oxo-4-oxazoline

4-Phenyl-2-oxo-4-oxazoline (1.61 g) and benzalacetone (1.46 g) were dissolved in acetonitrile (20 mL), and methanesulfonic acid (0.96 mL) was added. The obtained mixture was stirred at room temperature for 1 h and water (100 mL) and ethyl acetate (100 mL) were added to the reaction mixture. The organic layer was separated, washed twice with water (50 mL), and concentrated under reduced pressure to give an oily substance. The obtained oily substance was subjected to silica gel column chromatography and eluted with n-hexane-ethyl acetate (1:1). The solvent was evaporated and isopropyl ether (50 mL) was added to the obtained oily substance to allow crystallization and the mixture was stirred at room temperature for 1 h. The crystals were collected by filtration and washed with isopropyl ether (20 mL) to give the title compound (2.65 g; yield 86.3%) as white crystals.

Elemental analysis value for $C_{19}H_{17}NO_3$

Calculated: C,74.25; H,5.58; N,4.56. Found: C,74.28; H,5.72; N,4.52.

NMR(CDCl$_3$): 2.16 (3H, s), 3.02(1H, dd, J=17.7 and 6.0 Hz), 3.34(1H, dd, J=17.7 and 8.4 Hz), 4.67(1H, dd, J=8.4 and 6.0 Hz), 7.21–7.50(10H, m), 10.10(1H, s).

Example 5

Methyl 2-(4-(4-methoxyphenyl)-2-oxo-4-oxazolin-5-yl)propionate 4-(4-Methoxyphenyl)-2-oxo-4-oxazoline (1.00 g), methyl acrylate (0.94 mL) was dissolved in toluene (20 mL) and boron trifluoride etherate (1.31 mL) was added. The obtained mixture was heated to 90° C., and after stirring for 2 h, the solvent was concentrated under reduced pressure to give an oily substance. The obtained oily substance was subjected to silica gel column chromatography and eluted with n-hexane-ethyl acetate (1:1). The solvent was evaporated and the obtained oil was crystallized from ethanol. Isopropyl ether (10 mL) was added and the mixture was stirred at not higher than 5° C. for 1 h. The crystals were collected by filtration and washed with isopropyl ether to give the title compound (0.30 g; yield 20.7%) as gray-white crystals.

Elemental analysis value for $C_{14}H_{15}NO_5$

Calculated: C,60.64; H,5.45; N,5.05. Found: C,60.38; H,5.25; N,4.99.

NMR(CDCl$_3$): 2.68 (2H, t, J=7.7 Hz), 2.97(2H, t, J=7.7 Hz), 3.67(3H, s), 3.83(3H, s), 6.97 (2H, d, J=8.7 Hz), 7.38 (2H, d, J=8.7 Hz), 10.13(1H, s).

Example 6

Methyl 2-(4-(4-chorophenyl)-2-oxo-4-oxazolin-5-yl)propionate 4-(4-Chlorophenyl)-2-oxo-4-oxazoline (3.0 g) was dissolved in methanol (30 mL) and methyl acrylate (1.66 mL) and triethylamine (2.14 mL) were added. The obtained mixture was stirred with reflux for 6 h, and the solvent was concentrated under reduced pressure. Isopropanol (9 mL) and isopropyl ether (21 mL) were added, and the mixture was allowed to stand at room temperature overnight and was cooled to not higher than 5° C. and stirred for 1 h. The precipitated crystals were collected by filtration and washed with isopropyl ether to give the title compound (2.81 g; yield 65.0%).

Example 7

4-(4-Chlorophenyl-5-(1-methyl-3-oxobutyl)-2-oxo-4-oxazoline 4-(4-Chlorophenyl)-2-oxo-4-oxazoline (1.0 g) and 3-penten-2-one (0.75 mL) were dissolved in methanol (30 mL), and triethylamine (0.71 mL) was added. The mixture was stirred with reflux for 15 h. The reaction mixture was concentrated under reduced pressure and isopropyl ether (20 mL) was added to allow crystallization. The crystals were collected by filtration and washed with isopropyl ether to give the title compound (1.14 g; yield 79.7%) as pale-yellow-brown crystals.

Elemental analysis value for $C_{14}H_{14}NO_3Cl$

Calculated: C,60.11; H,5.04; N,5.01. Found: C,59.84; H,5.04; N,5.02.

NMR(CDCl$_3$): 1.27(3H, d, J=6.9 Hz), 2.17(3H, m), 2.71 (1H, dd, J=17.9 and 6.3 Hz), 2.96(1H, dd, J=17.9 and 7.6 Hz), 3.51–3.58(1H, m), 7.43–7.51(4H, m), 10.25(1H, s).

Example 8

Methyl 2-amino-4-(4-chlorophenyl)-5-oxazolepropionate

To a solution of 2-amino-4-(4-chlorophenyl)oxazole (584 mg) and methyl acrylate (0.81 mL) in dichloromethane (5.8 mL) was added dropwise titanium tetrachloride (TiCl$_4$) (0.99 mL) under ice-cooling. The obtained mixture was allowed to warm to room temperature and stirred for 6 h. The solvent was evaporated and water was added to the residue. The mixture was extracted with ethyl acetate, and the extract was washed with water and dried (MgSO$_4$). The solvent was evaporated and the residue was crystallized from isopropyl ether-ethyl acetate (209 mg; yield 51.3%). Recrystallization from isopropyl ether-ethyl acetate gave the title compound as pale-yellow crystals.

Elemental analysis value for $C_{13}H_{13}NClN_2O_3$

Calculated: C,55.62; H,4.67; N,9.98. Found: C,55.48; H,4.52; N,10.00.

NMR(CDCl$_3$): 2.67(2H, t, J=7.8 Hz), 3.09(2H, t, J=7.8 Hz), 3.68(3H, s), 4.69(2H, bs), 7.36(2H, d, J=8.6 Hz), 7.52(2H, d, J=8.6 Hz)

Example 9

Methyl 2-(4-(4-chlorophenyl)-2-oxo-4-oxazolin-5-yl)propionate 4-(4-chlorophenyl)-2-oxo-4-oxazoline (5.00 g) was suspended in acetonitrile (15 ml) in a reaction vessel, and the gas in the reaction vessel was substituted for nitrogen gas. The obtained suspension was cooled and conc. sulfuric acid (7.53 g) was added dropwise at 2–10° C. Then methyl acrylate (4.41 g) was added dropwise at 2–3° C. The obtained mixture was stirred at 20–30° C. for 1.5 h and methanol (15 ml) was added dropwise at 22–25° C. After cooling, water was added dropwise at 5–8° C. The precipitated crystals were collected by filtration, washed with water (25 ml), 1% aqueous sodium hydrogencarbonate (25 ml), water (25 ml) and diisopropyl ether (25 ml), and dried under reduced pressure at 40° C. for 7 h to give the title compound (5.72 g, yield 79.4%) as pale-red white crystals.

Example 10

Methyl 3-[2-oxo-4-(4-trifluoromethylphenyl)-4-oxazolin-5-yl]propionate

A mixture of 4-(4-trifluoromethylphenyl)-2-oxazolone (10.8 g), methyl acrylate (8.10 g), boron trifluoride diethyl ether complex (6.68 g) and toluene (50 mL) was stirred with heating under reflux for 3 h. The reaction mixture was concentrated and poured into iced water (200 mL). The precipitated solid was collected by filtration, washed with water and air-dried. Recrystallization from isopropyl alcohol-isopropyl ether gave the title compound as pale-yellow prism crystals (4.00 g, 27%). melting point: 156–157° C.

Example 11

Methyl 3-[2-oxo-4-(3',4'-dichlorophenyl)-4-oxazolin-5-yl]propionate

A mixture of 4-(3',4'-dichlorophenyl)-2-oxazolone (8.9 g), methyl acrylate (13.2 g), boron trifluoride diethyl ether complex (8.5 g) and toluene (100 mL) was stirred with heating under reflux for 12 h. The reaction mixture was concentrated and poured into iced water (500 mL). The precipitated solid was collected by filtration, washed with water and air-dried to give the title compound as crystals (9.0 g, 75%). Recrystallization from ethyl acetate-hexane gave pale-yellow prism crystals. melting points 129–130° C.

Reference Example 1

4-(4-Chlorophenyl)-2-oxo-4-oxazoline

To a mixture of 4'-chloro-2-hydroxyacetophenone (3.41 g), potassium cyanate (3.25 g) and isopropanol (15 mL) was added dropwise acetic acid (2.88 g) at 50° C. The obtained mixture was stirred at 50° C. for 5 h and water (34 mL) was added. The precipitated crystals were collected by filtration, and washed with water and then with isopropyl ether to give 4-(4-chlorophenyl)-2-oxo-4-oxazoline (3.33 g; yield 85.1%).

NMR(DMSO-$d_6$): 7.50(2H, d, J=8.6 Hz), 7.58(2H, d, J=8.6 Hz), 7.73(1H, s), 11.39(1H, bs)

Reference Example 2

4-Phenyl-2-oxo-4-oxazoline

In the same manner as in Reference Example 1, the title compound was obtained (yield 64.1%).

NMR(CDCl$_3$): 7.13(1H, s), 7.26–7.44(5H, m)

Reference Example 3

2-Amino-4-(4-chlorophenyl)oxazole

To a mixture of 4-chloro-2'-hydroxyacetophenone (17.06 g), cyanamide (5.04 g) and methanol (170 mL) was added dropwise 28% sodium methoxide under ice-cooling. The obtained mixture was allowed to warm to room temperature and stirred for 2 h. Water (34 mL) was added, and the mixture was extracted with ethyl acetate. The extract was washed with water and the solvent was evaporated. The residue was subjected to silica gel column chromatography and eluted with ethyl acetate-n-heptane (1:2) to give the title compound as yellow crystals (2.84 g; yield 14.6%). Recrystallization from ethyl acetate-n-heptane gave yellow crystals.

Elemental analysis value for $C_9H_7ClN_2O$

Calculated: C, 55.54; H, 3.63; N, 14.39. Found: C, 55.49; H, 3.61; N, 14.35

NMR(DMSO-$d_6$): 6.76(2H, bs), 7.42(2H, d, J=8.8 Hz), 7.65(2H, d, J=8.5 Hz), 7.92(1H, s)

Reference Example 4

Methyl 2-chloro-4-(4-chlorophenyl)-5-oxazolepropionate

To a mixture of methyl 4-(4-chlorophenyl)-2-oxo-4-oxazoline-5-propionate (823.7 g) and phosphorus oxychloride (1090 mL) was added pyridine (235.5 mL) and the mixture was stirred at 90° C. for 8 h and allowed to stand overnight at room temperature. A solution obtained by diluting the obtained mixture with acetonitrile (2471 mL) was added dropwise to water (8237 mL) at not higher than 35° C. Then water (4119 mL) was added and the precipitated crystals were collected by filtration to give the title compound (805.4 g, yield: 91.7%).

NMR(CDCl$_3$): 2.74 (2H, t, J=7.8 Hz), 3.19(2H, t, J=7.8 Hz), 3.69(3H, s),7.37–7.42(2H, m), 7.56–7.60(2H, m)

Reference Example 5

Methyl 4-(4-chlorophenyl)-2-(2-methylimidazol-1-yl)-5-oxazolepropionate

A mixture of methyl 2-chloro-4-(4-chlorophenyl)-5-oxazolepropionate (805.4 g), 2-methylimidazole (1101.7 g) and dimethyl sulfoxide (2416 mL) was stirred at 110° C. for 8 h and water was added to the obtained mixture. The mixture was extracted with ethyl acetate and the extract was washed with 5% brine. The solvent was evaporated and the residue was dissolved in ethyl acetate (1611 mL) with heating. n-Heptane (4832 mL) was added at 30° C. The precipitated crystals were collected by filtration and washed with ethyl acetate-n-heptane (1:3) to give the title compound (716.6 g, yield: 77.2%).

NMR(CDCl$_3$): 2.76–2.81(5H, m), 3.27(2H, t, J=7.6 Hz), 3.70(3H, s), 7.00(1H, d, J=1.7 Hz), 7.41–7.45(3H, m), 7.62–7.66(2H, m)

Reference Example 6

4-(4-Chlorophenyl)-5-(3-hydroxypropyl)-2-(2-methylimidazol-1-yl)oxazole

To a solution of methyl 4-(4-chlorophenyl)-2-(2-methylimidazol-1-yl)-5-oxazolepropionate (716.6 g) in toluene (7166 ml) was added dropwise sodium bis(2-methoxyethoxy)aluminum hydride (70% toluene solution, 957.6 g) at not higher than 5° C. over 4 h. To the reaction mixture was added dropwise 10% aqueous Rochelle salt solution (7166 ml) at not higher than 10° C. and the precipitated crystals were collected by filtration. The obtained crystals were washed with 10% Rochelle salt and water, and dried under reduced pressure. The residue was suspended in a mixture of ethyl acetate (717 mL) and isopropyl ether (2866 mL) and the suspension was stirred at room temperature for 3 h. The obtained crystals were collected by filtration to give the title compound (509 g, yield: 77.3%).

NMR(CDCl$_3$): 1.98–2.35(2H, m), 2.76(3H, s), 3.06(2H, t, J=7.7 Hz), 3.76(2H, t, J=6.0 Hz), 6.98(1H, d, J=1.5 Hz), 7.39–7.46(3H, m), 7.63–7.66(2H, m)

Reference Example 7

4-(4-Chlorophenyl)-2-(2-methylimidazol-1-yl)-5-(3-(2-methylphenoxy)propyl)oxazole To a solution of 4-(4-chlorophenyl)-5-(3-hydroxypropyl)-2-(2-methylimidazol-1-yl)oxazole (509 g), triethylamine (254.6 mL) in toluene (4072 mL) was added dropwise methanesulfonyl chloride (136.4 mL) at not higher than 10° C. Ten minutes later, o-cresol (248.0 mL) and tetrabutylammonium bromide (25.8 g) were added to the obtained mixture and a solution of NaOH (255 g) in water (1018 mL) was further added. The mixture was heated under reflux for 1 h. After cooling, the toluene layer was separated and washed with 1N aqueous NaOH solution (4072 mL×3) and then with 5% aqueous NaCl solution. The solvent was evaporated and the obtained crystals were recrystallized from ethanol-water (9:1) to give the title compound (595.6 g, yield: 91.2%).

NMR(CDCl$_3$): 2.24–2.31(5H, m), 2.75(3H, s), 3.18 (2H, t, J=7.6 Hz), 4.06(2H, t, J=5.7 Hz), 6.76(1H, d, J=8.1 Hz), 6.85–6.90(1H, m), 6.98 (1H, d, J=1.7 Hz), 7.11–7.17(2H, m), 7.33–7.36(2H, m), 7.41 (1H, d, J=1.6 Hz), 7.59–7.62 (2H, m)

Elemental analysis value for C$_{23}$H$_{22}$N$_3$O$_2$Cl

Calculated: C,67.73; H,5.44; N,10.30. Found: C,67.63; H,5.38; N,10.30.

Reference Example 8

Methyl 2-bromo-4-(4-chlorophenyl)-5-oxazolepropionate

To a solution of methyl 2-amino-4-(4-chlorophenyl)-5-oxazblepropionate (201 mg) in 48% aqueous HBr was added water (4 mL) and a solution of NaNO$_2$ (60 mg) in water (0.1 mL) was added dropwise under ice-cooling. After stirring the obtained mixture for 1 h, water was added and the mixture was extracted with ethyl acetate. The ethyl acetate layer was washed with water and the solvent was evaporated. The residue was subjected to silica gel chromatography and eluted with hexane-ethyl acetate (4:1) to give the title compound.

NMR(CDCl$_3$): 2.77 (2H, t, J=6.0 Hz), 3.18(2H, t, J=6.0 Hz), 3.71(3H, s), 7.48(2H, d, J=8.5 Hz), 7.99(2H, d, J=8.5 Hz)

Reference Example 9

4-(4-Chlorophenyl)-2-(2-methylimidazol-1-yl)-5-(3-(2-methylphenoxy)propyl)oxazole 4-(4-Chlorophenyl)-5-(3-hydroxypropyl)-2-(2-methylimidazol-1-yl)oxazole (10.00 g) was suspended in tetrahydrofuran (100 ml) and diisopropylethylamine (6.11 g) was added to the obtained suspension. Methanesulfonyl chloride (5.41 g) was added dropwise while maintaining the mixture at not higher than 10° C. The obtained mixture was stirred for 40 min and o-cresol (5.11 g) was added. NaOH (5.0 g) and tetrabutylammonium bromide (0.51 g) were dissolved in water (20 ml) and the obtained solution was added to the reaction mixture.

The obtained mixture was stirred with heating under reflux for 2 h, cooled to about 35° C. and separated. The organic layer was washed 3 times with 1N aqueous NaOH (50 ml) and once with 5% brine (50 ml) and concentrated under reduced pressure. To the concentration residue was added a mixture (25 ml) of methanol modified ethanol-ethyl acetate (1:1) and the mixture was dissolved by heating. The obtained solution was stirred at room temperature to allow crystallization, and the mixture was stirred at the same temperature for 1 h. Further, water (25 ml) was added dropwise and the mixture was stirred at not higher than 10° C. for 1 h. The crystals were collected by filtration, washed with a mixture (50 ml) of methanol modified ethanol-water (8:2) and a mixture (50 ml) of methanol modified ethanol-water (1:9), and dried under reduced pressure at 45° C. to give the title compound (11.31 g. yield 88.0%) as pale-yellow white crystals.

The obtained crystals (10.00 g) were dissolved in a mixture (40 ml) of methanol modified ethanol-water (9:1) by heating at about 70° C. Activated carbon (0.5 g) was added to the obtained solution and the mixture was stirred for 10 min. The activated carbon was removed by filtration and washed with a mixture (10 ml) of methanol modified ethanol-water (9:1). The filtrate was cooled to room temperature over about 1 h to allow crystallization, and the mixture was stirred further at not higher than 10° C. for 1 h. The precipitated crystals were collected by filtration and washed with a mixture (50 ml) of methanol modified ethanol-water (9:1) and water (50 ml), and dried under reduced pressure at 50° C. to give a pure product of the title compound (9.40 g, yield 94.0%) as nearly white crystals.

Reference Example 10

Unground crystals (30.804 kg) of 4-(4-chlorophenyl)-2-(2-methylimidazol-1-yl)-5-(3-(2-methylphenoxy)-propyl)oxazole were ground in a Jet Mill (Nippon Pneumatic Mfg. Co., Ltd.: PJM-100SP) using nitrogen gas (grinding pressure:3.08 kgf/cm$^2$) to give a ground product (30.401 kg, particle size: 2.7 μm (average particles)).

Reference Example 11

2-Hydroxy-4'-trifluoromethylacetophenone

A mixture of 2-bromo-4'-trifluoromethylacetophenone (40.0 g), sodium formate (40.0 g) and methanol (200 mL) was heated under reflux and stirred for 6 h. The reaction mixture was concentrated and poured into water (500 mL). The precipitated solid was collected by filtration, washed with water and air-dried to give the title compound as crystals (24.5 g, 80%). melting point: 112–114° C.

Reference Example 12

2-Oxo-2-(4-trifluoromethylphenyl)ethyl Phenylcarbonate

To a mixture of 2-hydroxy-4'-trifluoromethylacetophenone (24.0 g), pyridine (10.3 g) and tetrahydrofuran (200 mL) was added dropwise phenyl chlorocarbonate (20.4 g) under ice-cooling, and the mixture was stirred at room temperature for 1 h. The reaction mixture was concentrated, poured into water (500 mL) and extracted with ethyl acetate (150 mL×2). The organic layer was washed with water and then with saturated brine, dried over anhydrous magnesium sulfate and concentrated. To the residue was added isopropyl ether (100 mL) to allow crystallization to give the title compound as crystals (18.9 g, 53%). melting point: 134–135° C.

Reference Example 13

4-(4-Trifluoromethylphenyl)-2-oxazolone

A mixture of 2-oxo-2-(4-trifluoromethylphenyl)ethyl phenylcarbonate (18.0 g), ammonium acetate (20 g) and acetic acid (100 mL) was stirred with heating under reflux for 1 h. The reaction mixture was concentrated and poured into iced water (200 mL). The precipitated solid was collected by filtration, washed with water and air-dried to give the title compound as crystals (10.8 g, 85%). Decomposed at 250° C. or higher.

Reference Example 14

Methyl 2-chloro-4-(4-trifluoromethylphenyl)-5-oxazolepropionate

A mixture of methyl 3-[2-oxo-4-(4-ttrifluoromethylphenyl)-4-oxazolin-5-yl]propionate (3.90 g, phosphorus oxychloride (11.5 g) and pyridine (0.98 g) was heated to 100–105° C. and stirred for 1 h. The reaction mixture was added dropwise to warm water (100 mL, 30° C.), and the mixture was extracted with ethyl acetate (150 mL×2). The organic layer was washed with saturated brine (100 mL) and dried over anhydrous magnesium sulfate. The organic layer was concentrated and the residue was subjected to silica gel column chromatography and the title compound was obtained as a yellow oil (2.66 g, 64%) from an eluate from ethyl acetate-hexane (1:4, v/v).

NMR(CDCl$_3$)δ: 2.77(2H, t, J=7 Hz), 3.24(2H, t, J=7 Hz), 3.70(3H, s), 7.68(2H, d, J=8.5 Hz), 7.78(2H, d, J=8.5 Hz).

Reference Example 15

Methyl 2-(2-methyl-1-imidazolyl)-4-(4-trifluoromethylphenyl)-5-oxazolepropionate A mixture of methyl 2-chloro-4-(4-trifluoromethylphenyl)-5-oxazolepropionate (1.33 g), 2-methylimidazole (1.33 g), potassium carbonate (2.00 g) and N-methylpyrrolidone (10 mL) was stirred at 110° C. for 2 h. The reaction mixture was poured into iced water (100 mL), and the precipitated crystals were collected by filtration, washed with water and air-dried to give the title compound as crystals. Recrystallization from ethyl acetate-hexane gave pale-yellow prism crystals (1.07 g, 71%). melting point: 94–95° C.

Reference Example 16

2-(2-Methyl-1-imidazolyl)-4-(4-trifluoromethylphenyl)-5-oxazolepropanol

Methyl 2-(2-methyl-1-imidazolyl)-4-(4-trifluoromethylphenyl)-5-oxazolepropionate (1.00 g) was dissolved in toluene (15 mL). To the obtained solution was added dropwise a mixture of a 70% solution (1.20 g) of sodium bis(2-methoxyethoxy)aluminum hydride in toluene and toluene (5 mL) at 0° C., and the mixture was stirred at 0° C. for 30 min. To the reaction mixture was carefully added a 10% aqueous solution (50 mL) of potassium sodium (+)-tartrate tetrahydrate, and the mixture was stirred at room temperature for 1 h. The precipitated crystals were collected by filtration, washed successively with a 10% aqueous solution of potassium sodium (+)-tartrate tetrahydrate, pure water and isopropyl ether, and air-dried to give the title compound as crystals (0.75 g, 81%). Recrystallization from ethyl acetate-isopropyl ether gave pale-yellow prism crystals. melting point: 127–129° C.

Reference Example 17

2-(2-Methyl-1-imidazolyl)-5-[3-(2-methylphenoxy)propyl]-4-(4-trifluoromethylphenyl)oxazole To a mixture of 2-(2-methyl-1-imidazolyl)-4-(4-trifluoromethylphenyl)-5-oxazolepropanol (700 mg), 2-methylphenol (432 mg), tributylphosphine (607 mg) and tetrahydrofuran (10 mL) was added 1,1'-(azodicarbonyl) dipiperidine (750 mg) at room temperature and the mixture was stirred for 1 h. The reaction mixture was concentrated and the residue was subjected to silica gel column chromatography. The title compound was obtained as crystals from an eluate from ethyl acetate-hexane (2:3, v/v). Recrystallization from acetone-isopropyl ether gave colorless prism crystals (591 mg, 67%). melting point: 101–102° C.

Reference Example 18

2-Hydroxy-3',4'-dichloroacetophenone

A mixture of 2-bromo-3',4'-dichloroacetophenone (78.0 g), sodium formate (68.0 g) and methanol (300 mL) was heated under reflux and stirred for 16 h. The reaction mixture was concentrated and poured into water (1 L). The precipitated solid was collected by filtration, washed with water and then with isopropyl ether, air-dried, and further dried under reduced pressure at 40° C. to give the title compound as crystals (25.0 g, 42%). Recrystallization from ethyl acetate-hexane gave pale-yellow prism crystals. melting point: 115–118° C.

Reference Example 19

4-(3,4-Dichlorophenyl)-2-oxazolone

A mixture of 2-hydroxy-3',4'-dichloroacetophenone (10.3 g), potassium cyanate (8.1 g) and 2-propanol (100 mL) was heated to 50° C., and acetic acid (6.0 g) was slowly added dropwise. The mixture was stirred at 50° C. for 2 h. The reaction mixture was concentrated and poured into iced water (200 mL). The precipitated solid was collected by filtration, washed with water and air-dried to give the title compound as crystals (6.0 g, 52%). Recrystallization from tetrahydrofuran-hexane gave pale-yellow prism crystals. melting point: 262–263° C.

Reference Example 20

Methyl 2-chloro-4-(3,4-dichlorophenyl)-5-oxazolepropionate

A mixture of methyl 3-[4-(3,4-dichlorophenyl)-2-oxo-4-oxazolin-5-yl]propionate (9.0 g), phosphorus oxychloride (26.2 g) and pyridine (2.25 g) was heated to 100–105° C. and stirred for 1 h. The reaction mixture was added dropwise to warm water (100 mL, 30° C.) and extracted with ethyl acetate (150 mL×2). The organic layer was washed with saturated brine (100 mL) and dried over anhydrous magnesium sulfate. The organic layer was concentrated and the residue was subjected to silica gel column chromatography. The title compound was obtained as a yellow oil (5.00 g, 52%) from an eluate from ethyl acetate-hexane (1:4, v/v).

NMR(CDCl$_3$)δ: 2.76(2H, t, J=7 Hz), 3.20(2H, t, J=7 Hz), 3.70(3H, s), 7.49(2H, d, J=1 Hz), 7.79(1H, d, J=1 Hz).

Reference Example 21

Methyl 4-(3,4-dichlorophenyl)-2-(2-methyl-1-imidazolyl)-5-oxazolepropionate

A mixture of methyl 2-chloro-4-(3,4-dichlorophenyl)-5-oxazolepropionate (1.00 g), 2-methylimidazole (0.82 g), potassium carbonate (0.69 g) and N,N-dimethylformamide (20 mL) was stirred at 120° C. for 1 h. The reaction mixture was poured into iced water (100 mL) and the precipitated crystals were collected by filtration, washed with water and then with isopropyl ether and air-dried to give the title compound as crystals. Recrystallization from ethyl acetate-isopropyl ether gave pale-yellow prism crystals (0.82 g, 72%). melting point: 116–117° C.

Reference Example 22

4-(3,4-Dichlorophenyl)-2-(2-methyl-1-imidazolyl)-5-oxazolepropanol

Methyl 4-(3,4-dichlorophenyl)-2-(2-methyl-1-imidazolyl)-5-oxazolepropionate (0.67 g) was dissolved in toluene (5 mL). To the obtained solution was added dropwise a mixture of a 70% solution (0.81 g) of sodium bis(2-methoxyethoxy)aluminum hydride in toluene and toluene (2 mL) at 0° C. and the mixture was stirred at 0° C. for 1 h. To the reaction mixture was carefully added a 10% aqueous solution (50 mL) of potassium sodium (+)-tartrate tetrahydrate and the mixture was stirred at room temperature for 1 h. The precipitated crystals were collected by filtration, washed successively with a 10% aqueous solution of potassium sodium (+)-tartrate tetrahydrate, pure water and isopropyl ether, and air-dried to give the title compound as crystals (0.46 g, 74%). Recrystallization from acetone-hexane gave pale-yellow prism crystals. melting point: 140–141° C.

Reference Example 23

4-(3,4-Dichlorophenyl)-2-(2-methyl-1-imidazolyl)-5-[3-(2-methylphenoxy)propyl]oxazole To a mixture of 4-(3,4-dichlorophenyl)-2-(2-methyl-1-imidazolyl)-5-oxazolepropanol (352 mg), 2-methylphenol (216 mg), tributylphosphine (405 mg) and tetrahydrofuran (10 mL) was added 1,1'-(azodicarbonyl)dipiperidine (450 mg) at room temperature, and the mixture was stirred for 1 h. The reaction mixture was concentrated and the residue was subjected to silica gel column chromatography. The title compound was obtained as crystals from an eluate from ethyl acetate-hexane (2:3, v/v). Recrystallization from acetone-isopropyl ether gave colorless prism crystals (271 mg, 61%). melting point: 116–117° C.

Reference Example 24

4-(4-Chlorophenyl)-2-(2-methyl-1-imidazolyl)-5-(3-(2-methylphenoxy)propyl)oxazole Hydrochloride To a mixture of 4-(4-chlorophenyl)-2-(2-methyl-1-imidazolyl)-5-(3-(2-methylphenoxy)propyl)oxazole (1.0 g) and acetone (10 ml) was added conc. hydrochloric acid (0.3 ml) and the mixture was stood at room temperature. The precipitated crystals were collected by filtration (0.97 g). Recrystallization from ethanol gave the title compound.

Elemental analysis value for $C_{23}H_{22}ClN_3O \cdot HCl \cdot 1/3H_2O$

Calculated: C, 61.35; H, 5.30; N. 9.33. Found: C, 61.61; H, 5.24; N, 9.37.

NMR(CDCl$_3$)δ: 2.20(3H, s), 2.25–2.38(2H, m), 3.17(3H, s), 3.25(2H, t, J=7.2 Hz), 4.08(2T, t, J=5.2 Hz), 6.76(1H, d, J=8.2 Hz), 6.88(1H, t, J=7.2 Hz), 7.13(2H, t, J=7.2 Hz), 7.37–7.43(3H, m), 7.52–7.61(3H, m).

INDUSTRIAL APPLICABILITY

According to the production method of the present invention, a carbon-carbon bond can be directly formed on oxazole unsubstituted at the 5-position. The present invention provides an industrially advantageous, economical, easy and convenient production method for forming a carbon-carbon bond at the 5-position of oxazole. In addition, according to the production method of the present invention, introduction of a carbon substituent before constructing an oxazole ring is not necessary. Consequently, various 5-substituted oxazole derivatives can be synthesized without limitation on a starting material.

What is claimed is:

1. A method of producing a compound represented by the formula

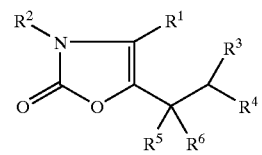

wherein
$R^1$ and $R^2$ are each a hydrogen atom, an optionally substituted hydrocarbon group or an optionally substituted heterocyclic group,
$R^3$ is an electron-withdrawing group, and
$R^4$ $R^5$ and $R^6$ are each a hydrogen atom or an optionally substituted hydrocarbon group, or a salt thereof, which method comprises reacting a compound represented by the formula

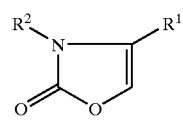

wherein the symbols in the formula are as defined above, or a salt thereof, with a compound represented by the formula

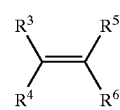

wherein the symbols in the formula are as defined above, or a salt thereof, in the presence of an acid or a base.

2. The production method of claim 1, wherein $R^1$ and $R^2$ are each a hydrogen atom, an optionally substituted alkyl group, an optionally substituted aralkyl group, an optionally substituted aryl group or an optionally substituted heterocyclic group.

3. The production method of claim 1, wherein $R^1$ is an optionally substituted aryl group or an optionally substituted aromatic heterocyclic group.

4. The production method of claim 1, wherein $R^1$ is an optionally substituted phenyl group.

5. The production method of claim 1, wherein $R^2$ is a hydrogen atom.

6. The production method of claim herein $R^4$, $R^5$ and $R^6$ are each a hydrogen atom, an optionally substituted alkyl group or an optionally substituted aryl group.

7. The production method of claim 1, wherein $R^4$, $R^5$ and $R^6$ are each a hydrogen atom.

8. The production method of claim 1, wherein $R^3$ is —CN, —COOR$^7$ ($R^7$ is a hydrogen atom or an optionally substituted hydrocarbon group) or —COR$^8$ ($R^8$ is a hydrogen atom, an optionally substituted hydrocarbon group or an optionally substituted heterocyclic group).

9. The production method of claim 1, wherein $R^3$ is —CN.

10. The production method of claim 1, wherein $R^3$ is —COOR$^7$ ($R^7$ is a hydrogen atom or an optionally substituted alkyl group).

11. The production method of claim 1, wherein $R^3$ is —COR$^8$ ($R^8$ is a hydrogen atom, an optionally substituted alkyl group or an optionally substituted aryl group).

12. The production method of claim 1, wherein the reaction is carried out in the presence of an acid.

13. A method of producing a compound represented by the formula

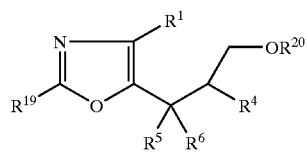

wherein $R^1$ is a hydrogen atom, an optionally substituted hydrocarbon group or an optionally substituted heterocyclic group, $R^4$, $R^5$ and $R^6$ are each a hydrogen atom or an optionally substituted hydrocarbon group, $R^{19}$ is an optionally substituted heterocyclic group containing nitrogen, which is bonded via a nitrogen atom, and $R^{20}$ is an optionally substituted hydrocarbon group, or a salt thereof, which method comprises reacting a compound represented by the formula

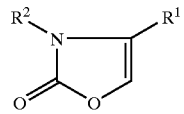

wherein $R^2$ is a hydrogen atom, an optionally substituted hydrocarbon group or an optionally substituted heterocyclic group, and the other symbol is as defined above, or a salt thereof, with a compound represented by the formula

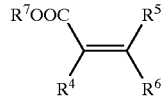

wherein $R^7$ is a hydrogen atom or an optionally substituted hydrocarbon group, and other symbols are as defined above, or a salt thereof, in the presence of an acid or a base to give a compound represented by the formula

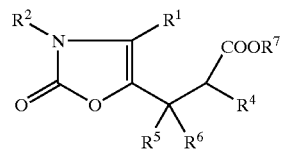

wherein the symbols in the formula are as defined above, or a salt thereof, subjecting this compound to halogenation reaction to give a compound represented by the formula

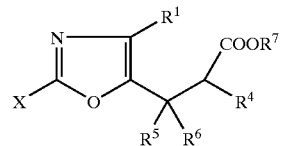

wherein X is a halogen atom, and other symbols are as defined above, or a salt thereof, reacting this compound with a compound represented by the formula: $R^{19}$—H [$R^{19}$ is as defined above] to give a compound represented by the formula

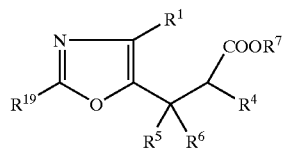

wherein the symbols in the formula are as defined above, or a salt thereof, subjecting this compound to a reduction reaction to give a compound represented by the formula

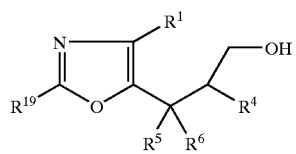

wherein the symbols in the formula are as defined above, or a salt thereof, reacting this compound with a compound represented by the formula: $R^{10}SO_2Cl$ [$R^{10}$ is an optionally substituted alkyl group or an optionally substituted aryl group] or a halogenating agent to give a compound represented by the formula

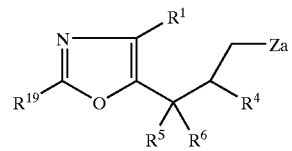

wherein Za is a halogen atom or —OSO$_2R^{10}$ ($R^{10}$ is as defined above), and other symbols are as defined above, or a salt thereof, and reacting this compound with a compound represented by the formula: $R^{20}$—OH [$R^{20}$ is as defined above].

* * * * *

UNITED STATES PATENT AND TRADEMARK OFFICE
CERTIFICATE OF CORRECTION

PATENT NO.     : 6,699,995 B1
DATED          : March 2, 2004
INVENTOR(S)    : Hiroyuki Tawada et al.

It is certified that error appears in the above-identified patent and that said Letters Patent is hereby corrected as shown below:

Column 30,
Line 63, change "...method of claim herein..." to -- ...method of claim 1, wherein... --.

Signed and Sealed this

Nineteenth Day of July, 2005

JON W. DUDAS
*Director of the United States Patent and Trademark Office*